(12) United States Patent
Lorente Bonde-Larsen et al.

(10) Patent No.: US 9,422,228 B2
(45) Date of Patent: Aug. 23, 2016

(54) PROCESS FOR THE PREPARATION OF OPTICALLY PURE FESOTERODINE DERIVATIVES

(71) Applicant: CRYSTAL PHARMA, S.A.U., Boecillo-Valladolid (ES)

(72) Inventors: Antonio Lorente Bonde-Larsen, Boecillo-Valladolid (ES); Francisco Javier Gallo Nieto, Boecillo-Valladolid (ES); Juan José Ferreiro Gil, Boecillo-Valladolid (ES); Pablo Martín Pascual, Boecillo-Valladolid (ES)

(73) Assignee: CRYSTAL PHARMA, S.A.U., Boecillo-Valladolid (ES)

( * ) Notice: Subject to any disclaimer, the term of this patent is extended or adjusted under 35 U.S.C. 154(b) by 0 days.

(21) Appl. No.: 14/398,718

(22) PCT Filed: Apr. 26, 2013

(86) PCT No.: PCT/EP2013/058756
§ 371 (c)(1),
(2) Date: Nov. 3, 2014

(87) PCT Pub. No.: WO2013/113946
PCT Pub. Date: Aug. 8, 2013

(65) Prior Publication Data
US 2015/0094485 A1 Apr. 2, 2015

(30) Foreign Application Priority Data

May 4, 2012 (WO) ............... PCT/EP2012/058234

(51) Int. Cl.
*C07C 229/00* (2006.01)
*C07C 213/08* (2006.01)
(Continued)

(52) U.S. Cl.
CPC ........... *C07C 213/08* (2013.01); *C07C 213/06* (2013.01); *C07C 225/16* (2013.01);
(Continued)

(58) Field of Classification Search
CPC . C07C 229/38; C07C 213/08; C07C 213/06; C07C 219/28; C07C 227/16; C07C 227/18; C07C 227/34; C07C 215/54; C07C 2101/14; C07C 225/16
See application file for complete search history.

(56) References Cited

U.S. PATENT DOCUMENTS 5,559,269 A 9/1996 Johansson et al.
6,858,650 B1 2/2005 Meese
(Continued)

FOREIGN PATENT DOCUMENTS

EP 1289929 B1 8/2007
EP 2338871 B1 9/2013
(Continued)

OTHER PUBLICATIONS

International Search Report dated Aug. 5, 2013 for PCT Application PCT/EP2013/058756.
(Continued)

*Primary Examiner* — Yevegeny Valenrod
*Assistant Examiner* — Blaine G Doletski
(74) *Attorney, Agent, or Firm* — Knobbe, Martens, Olson & Bear, LLP

(57) ABSTRACT

3,3-diphenylpropylamines of general formula (I), particularly Fesoterodine, as well as their enantiomers, solvates and salts, can be produced by treating a compound of formula (II) with a chiral alcohol to yield the diastereomeric esters of formula (IV) and (IV'), which can be further transformed into a compound of formula (I), or an enantiomer, solvate or salt thereof, wherein R1 is C1-C8 alkyl; and R2 and R3, independently of one another, represent H or C1-C6 alkyl, or together form a ring of 3 to 7 members with the nitrogen to which they are bound.

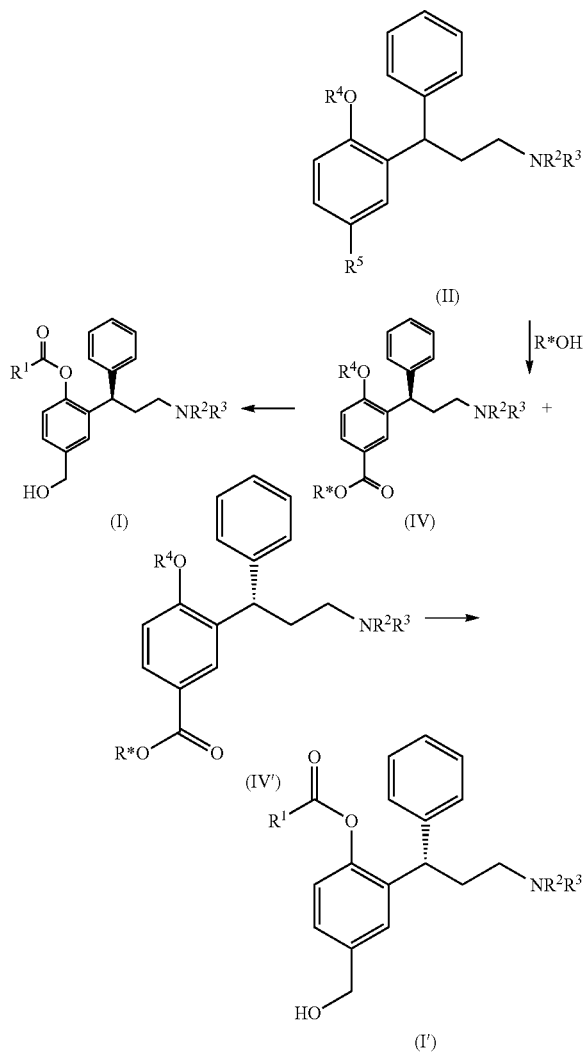

23 Claims, No Drawings

(51) Int. Cl.
*C07C 213/06* (2006.01)
*C07C 227/16* (2006.01)
*C07C 227/18* (2006.01)
*C07C 227/34* (2006.01)
*C07C 229/38* (2006.01)
*C07C 225/16* (2006.01)

(52) U.S. Cl.
CPC .......... *C07C227/16* (2013.01); *C07C 227/18* (2013.01); *C07C 227/34* (2013.01); *C07C 229/38* (2013.01); *C07C 2101/14* (2013.01)

(56) References Cited

U.S. PATENT DOCUMENTS

| | | | |
|---|---|---|---|
| 7,384,980 B2 | 6/2008 | Meese et al. | |
| 2011/0105783 A1* | 5/2011 | Mantegazza | C07C 219/30 560/42 |

FOREIGN PATENT DOCUMENTS

| | | |
|---|---|---|
| EP | 2281801 B1 | 1/2014 |
| GB | 948 583 A | 2/1964 |
| WO | 99/58478 A1 | 11/1999 |
| WO | 2007/138440 A1 | 12/2007 |
| WO | 2011/145019 A1 | 11/2011 |
| WO | 2011/158257 A1 | 12/2011 |
| WO | 2012/098560 A2 | 7/2012 |
| WO | 2013/113946 A2 | 8/2013 |

OTHER PUBLICATIONS

Nilvebrant et al. "Antimuscarinic Potency and Bladder Selectivity of PNU-200577, a Major Metabolite of Tolterodine", Pharmacol. Toxicol, 1997, 81 (4). 169-172.

Yoon, N.M. et al., "Seelective Reductions. XIX. The Rapid Reaction of Carboxylic Acids with Borane-Tetrahydrofuran. A Remarkably Convenient Procedure for the Selective Conversion of Carboxylic Acids to the Corresponding Alcohols in the Presence of Other Functional Groups," J. Org. Chem. 38, 2786 (1973).

Braun, L.M., "Ketenes. XIII. Reactions of Ketenes with Heterocumules," et al., J. Org. Chem., 36, 2388 (1971).

* cited by examiner

PROCESS FOR THE PREPARATION OF OPTICALLY PURE FESOTERODINE DERIVATIVES

CROSS REFERENCE TO RELATED APPLICATIONS

This application is the U.S. National Phase of International Application No. PCT/EP2013/058756, filed Apr. 26, 2013, designating the U.S. and published in English as WO 2013/113946 on Aug. 8, 2013 which claims the benefit of International Patent Application No. PCT/EP2012/058234, filed May 4, 2012.

FIELD OF THE INVENTION

The invention relates to a process for obtaining optically active 3,3-diphenylpropylamines, particularly Fesoterodine, as well as their enantiomers, solvates and salts. The invention is also directed to intermediate compounds useful in said process.

BACKGROUND OF THE INVENTION 3,3-diphenylpropylamines which act as muscarinic receptor antagonists and are useful in the treatment of urinary incontinence and other symptoms of urinary bladder hyperactivity are known. Said compounds include N,N-diisopropyl-3-(2-hydroxy-5-methylphenyl)-3-phenylpropylamine, the (R) enantiomer of which is known as Tolterodine.

Another compound with a similar structure is 5-hydroxymethyl tolterodine, which is the main metabolite of Tolterodine (Nilvebrant et al. *Pharmacol. Toxicol,* 1997, 81(4), 169-172), a potent muscarinic receptor antagonist (WO 94/11337).

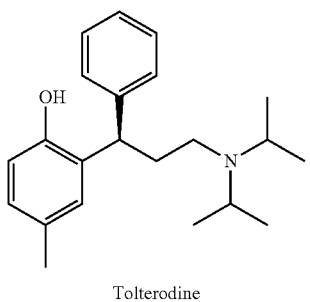

Tolterodine

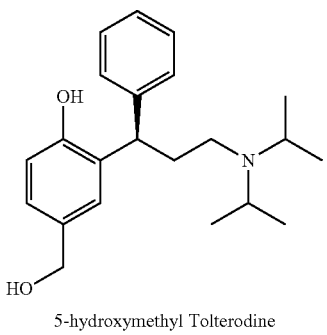

5-hydroxymethyl Tolterodine

WO 99/058478 describes the therapeutic usefulness of phenolic esters of said main metabolite of Tolterodine, especially of isobutyric acid 2-((R)-3-N,N-diisopropylamino-1-phenylpropyl)-4-(hydroxymethyl)phenyl ester, known as Fesoterodine. Said document also describes the formation of their salts, particularly, the formation of Fesoterodine fumarate.

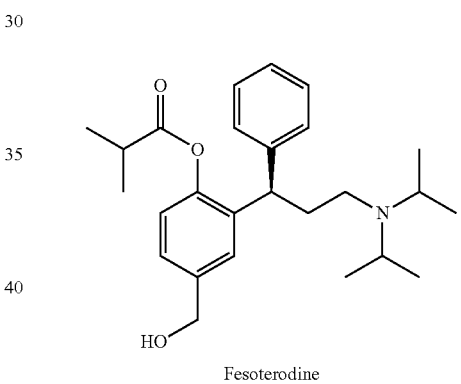

Fesoterodine

U.S. Pat. No. 5,559,269 discloses the preparation of 5-hydroxymethyl tolterodine and Fesoterodine through a very long synthesis process. The required chirality is introduced in step 3 by resolution of intermediate N,N'-diisopropyl-3-(2-benzyloxy-5-bromophenyl)-3-phenylpropyl amine (1) with tartaric acid.

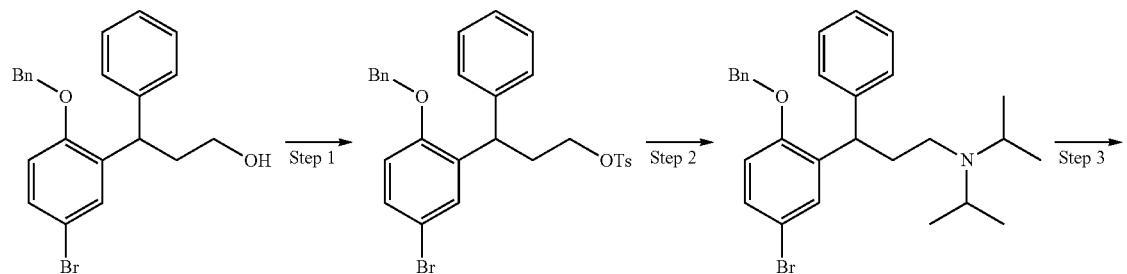

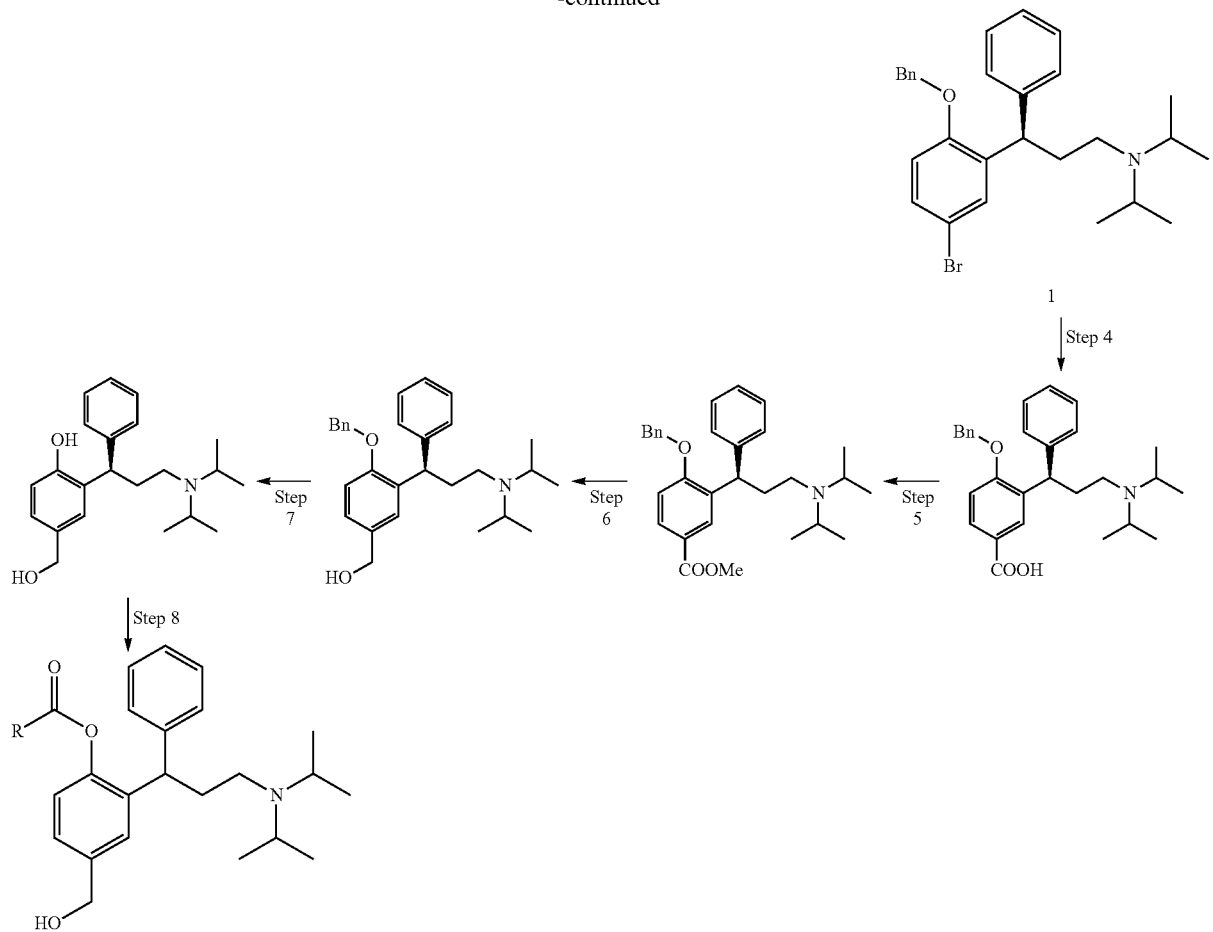
An alternative process for preparing chiral intermediate (1) is described in WO 99/58478. This process comprises the asymmetric addition of phenyl magnesium bromide to a chiral α,β-unsaturated amide.
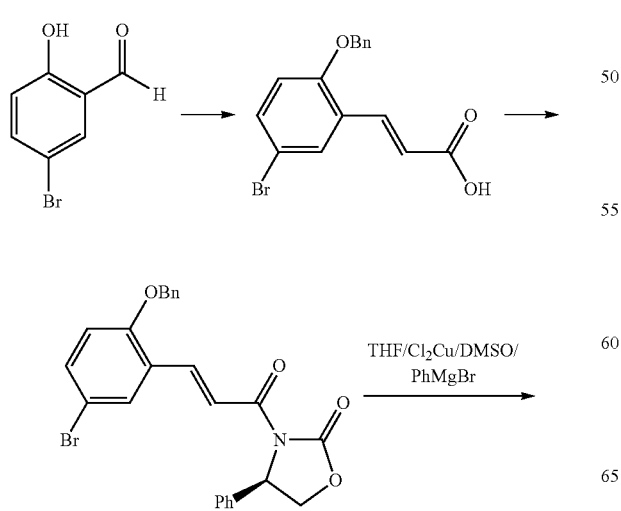
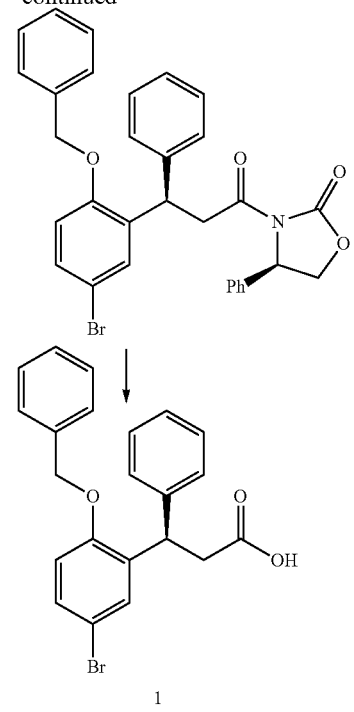

Compound (1) is obtained through long and cost-inefficient processes that require the use of expensive chiral reagents, which make it a non-suitable intermediate for the preparation of Fesoterodine and related compounds.

A different approach is described in EP 1289929 B1, by means of a synthetic route in which a coupling in acid medium is initially performed, forming a dihydrocoumarin as a racemic intermediate. Said intermediate is then subjected to a stereoselective resolution process to obtain the suitable enantiomer. The latter is subsequently reduced to a lactol derivative, in which a diisoalkylamine is introduced by means of a reductive amination. Although the process is shorter, many synthesis steps are still required. In addition, the use of the aluminum tert-butoxide as a reducing agent is a considerable problem of toxicity and added cost to the process.

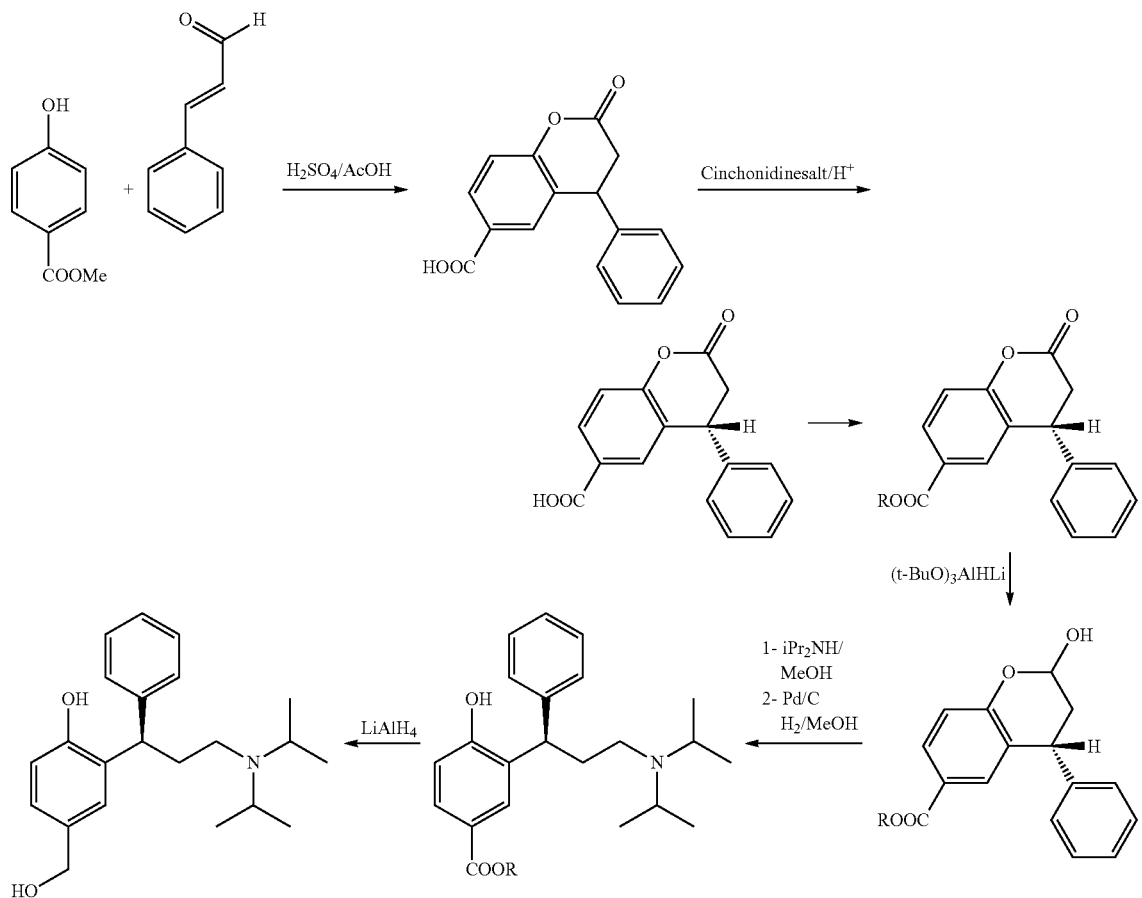

WO 2007/138440 describes a route of synthesis through the formation of a dihydrocoumarin intermediate, by means of a reaction needing conditions of reflux in toluene and toluene/hydrochloric acid for long time periods and with a low yield.

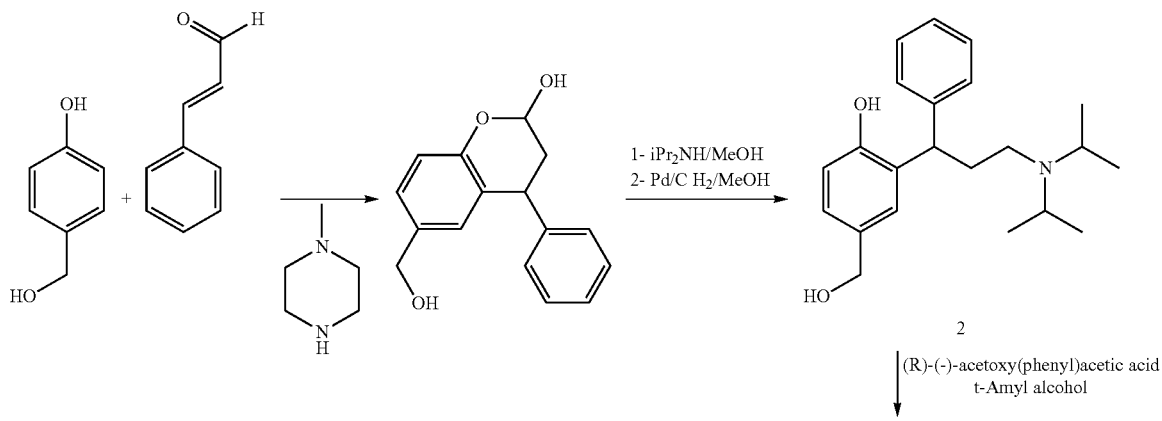

-continued

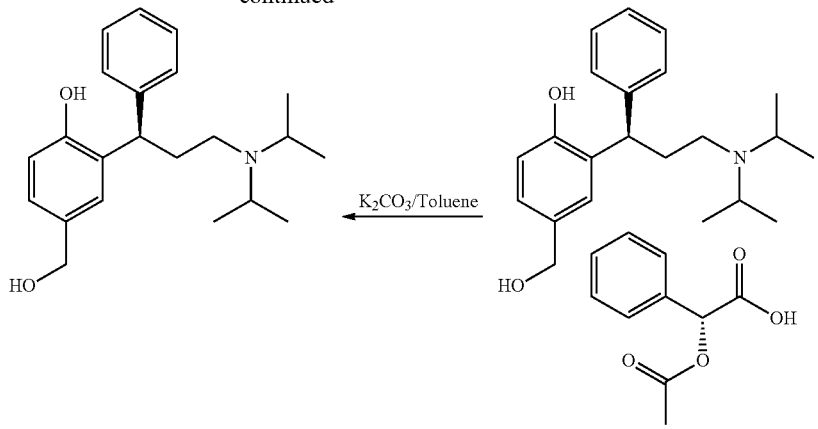

Optical resolution is performed on compound N,N'-disiopropyl-3-(2-hydroxy-5-hydroxymethyl-phenyl)-3-phenyl-propyl amine (2), which is the last intermediate of the synthesis, leading to more than 60% product loss at this point and, thus, making it a very expensive process. WO 2011/158257 refers to the optical resolution of compound (2) with D-(+)-maleic acid and consequently also has the same disadvantages.

US 2011/105783 and WO 2011/145019 refer to the resolution of intermediate N,N'-diisopropyl-3-(2-hydroxy-5-methylcarboxylate-phenyl)-3-phenylpropyl amine (3) with camphorsulfonic or dibenzoyltartaric acid.

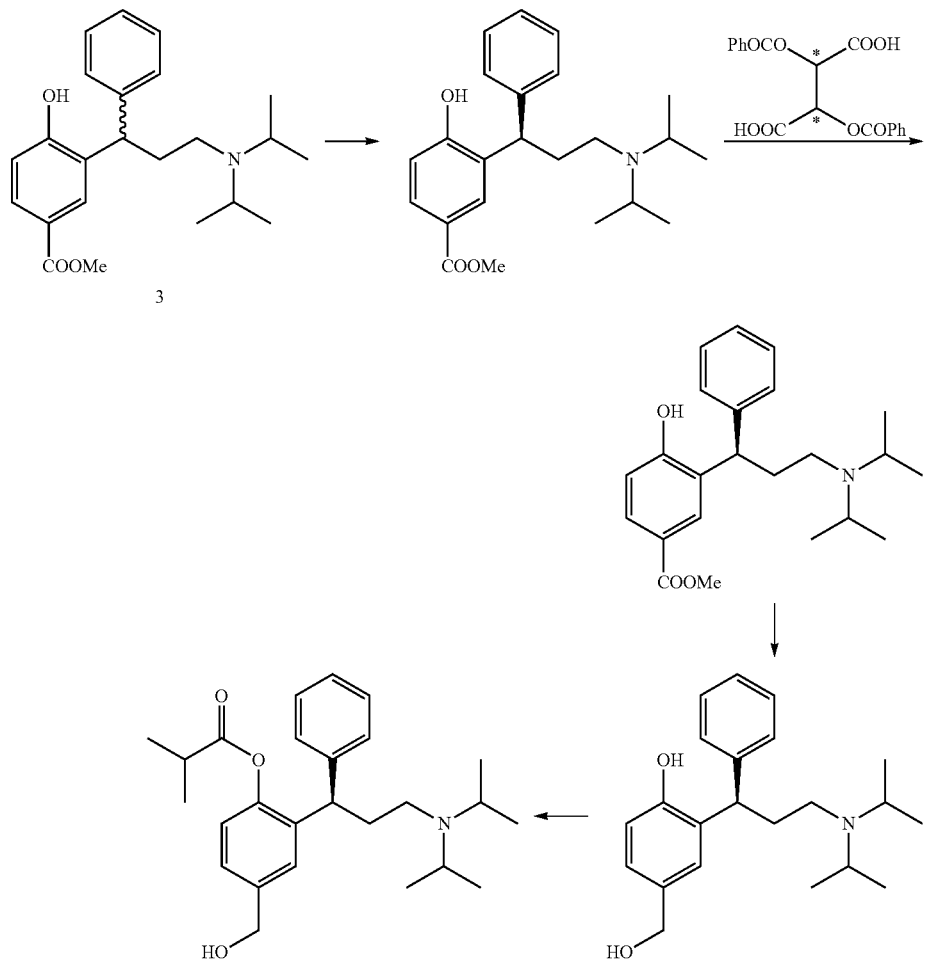

In the reported cases, processes based on optical resolution through formation of diastereomeric salts do not typically give rise to the chiral salts in a suitable diastereomeric excess, making necessary to further purify the compound by subsequent recrystallizations.

Furthermore, an additional step to cleave the diastereomeric salt and recover the desired enantiomer, which is further transformed into the final product, is required.

In view of the above, it is still necessary to provide an alternative process for obtaining optically active intermediates for the preparation of Fesoterodine and related 3,3-diphenylpropylamines.

GB 948,583 discloses the resolution of racemic 7-methoxy-1,2,3,4,4a,9,10,10a-octahydro-phenanthrene-carboxylic acid by transformation into the corresponding acid chloride, treatment with L-menthol and separation of the resulting diastereomeric compounds.

SUMMARY OF THE INVENTION

The invention faces the problem of providing a process for obtaining optically active 3,3-diphenylpropylamines, and particularly Fesoterodine, which overcomes all or part of the problems existing in the different aforementioned syntheses of the state of the art.

The solution provided by the present invention is based on the fact that compounds of formula (II)

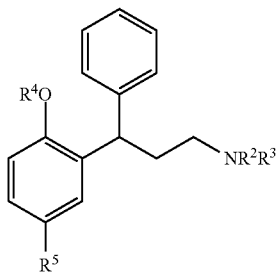

(II)

can be efficiently resolved into the corresponding diastereomeric esters of formula (IV) and (IV')

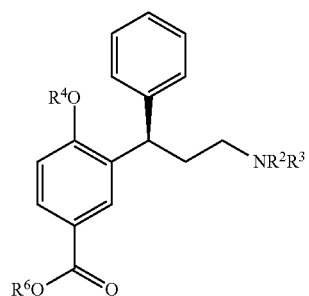

(IV)

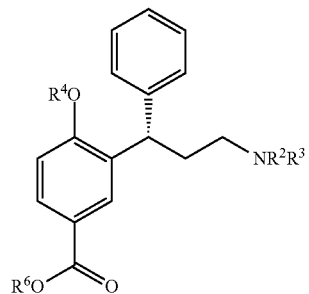

(IV')

by treatment with an optically active chiral alcohol of formula $R^6$—OH. Compounds (IV) and (IV') can be further transformed into 3,3-diphenylpropylamines, such as Fesoterodine.

Therefore, in one aspect the invention relates to a process for preparing a compound of formula (I) or (I'), or a solvate or salt thereof, which comprises:

(a) reacting a compound of formula (II), or a solvate or salt thereof, with an optically active chiral alcohol to yield compounds of formula (IV) and (IV'), or a solvate or salt thereof, and (b) converting the compound of formula (IV) or (IV'), or a solvate or salt thereof, into a compound of formula (I) or (I'), respectively, or a solvate or salt thereof.

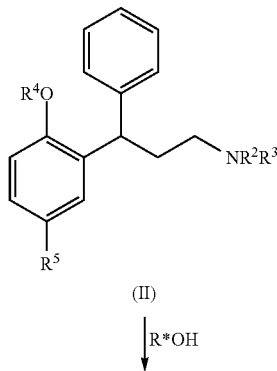

(II)

↓ R*OH

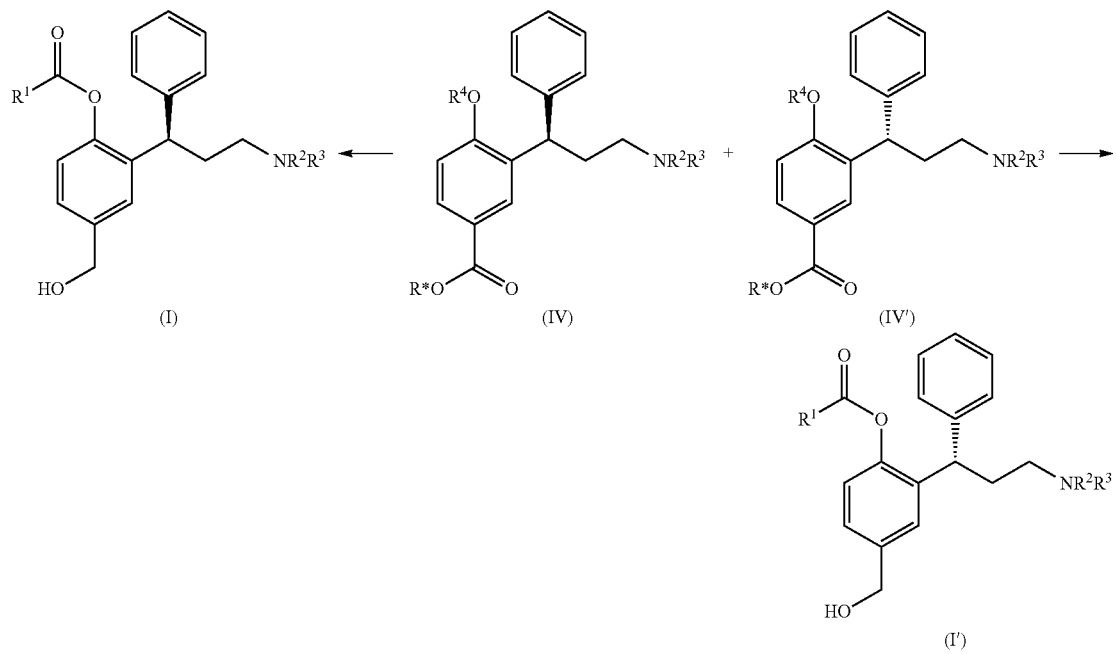

In another aspect, the invention relates to compounds that are intermediates in the process of the invention, such as compound of formula (IIa) and the diastereomeric esters of formula (IV) and (IV'), and solvates and salts thereof

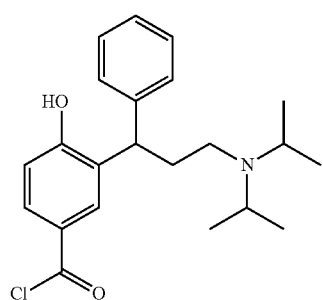

(IIa)

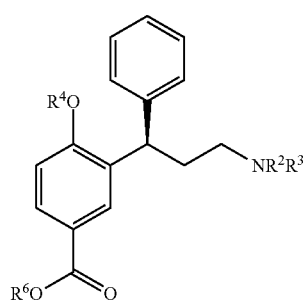

(IV)

DETAILED DESCRIPTION OF THE INVENTION

Definitions

As used herein, the term "alkyl" refers to a linear or branched alkane derivative containing from 1 to 6 ("$C_1$-$C_6$ alkyl"), preferably from 1 to 3 ("$C_1$-$C_3$ alkyl"), carbon atoms and which is bound to the rest of the molecule through a single bond. Illustrative examples of alkyl groups include methyl, ethyl, n-propyl, isopropyl, n-butyl, iso-butyl, tert-butyl, pentyl, hexyl, etc.

The term "haloalkyl" refers to an alkyl group as defined above wherein at least one of the hydrogen atoms has been substituted with a halogen group, for example $CF_3$, $CCl_3$, $CHF_2$, $CF_2CF_3$, etc.

The term "aryl" refers to an aromatic group having between 6 and 18, preferably between 6 and 10, more preferably 6 or 10 carbon atoms, comprising 1, 2 or 3 aromatic nuclei bound through a carbon-carbon bond or fused to one another. Illustrative examples of aryl groups include phenyl, naphthyl, biphenyl, indenyl, phenanthryl, etc.

The term "arylalkyl" refers to an alkyl group as defined above substituted with an aryl group as defined above, such as ($C_6$-$C_{18}$)aryl($C_1$-$C_6$)alkyl, ($C_6$-$C_{10}$)aryl($C_1$-$C_6$)alkyl and ($C_6$-$C_{10}$)aryl($C_1$-$C_3$)alkyl. Examples of such groups include benzyl, phenylethyl, phenylpropyl, naphthylmethyl, etc.

The term "cycloalkyl" refers to a radical derived from cycloalkane containing from 3 to 7 ("$C_3$-$C_7$ cycloalkyl"), preferably from 3 to 6 ("$C_3$-$C_6$ cycloalkyl") carbon atoms. Illustrative examples of cycloalkyl groups include cyclopropyl, cyclobutyl, cyclopentyl, cyclohexyl, etc.

The term "halogen" refers to bromine, chlorine, iodine or fluorine.

"Heterocyclyl" refers to a stable cyclic radical of 3 to 10 members, preferably a cycle of 5 or 6 members consisting of carbon atoms and from 1 to 5, preferably from 1 to 3, heteroatoms selected from nitrogen, oxygen and sulfur, and which may be completely or partially saturated or be aromatic ("heteroaryl"). In the present invention, the heterocyclyl can be a mono-, bi- or tricyclic system which may include fused ring systems. Illustrative examples of heterocyclyl groups include, for example, pyrrolidine, piperidine, piperazine, morpholine, tetrahydrofuran, benzimidazole, benzothiazole, furan, pyrrole, pyridine, pyrimidine, thiazole, thiophene, imidazole, indole, etc.

As understood in this technical area, there may be a certain degree of substitution in the aforementioned radicals. Therefore, there may be substitution in any of the groups of the present invention. The previous groups can be substituted in one or more available positions with one or more substituents. Said substituents include, for example and in non-limiting sense, $C_{1-6}$ alkyl, $C_{3-7}$ cycloalkyl, aryl, heterocyclyl, heteroaryl, halogen, —CN, $NO_2$, $CF_3$, —N($R_a$)($R_b$), —$OR_c$, —$SR_d$, —C(O)$R_e$, —C(O)$OR_f$, —C(O)N($R_g$)($R_h$), —OC(O)$R_i$; wherein $R_a$, $R_b$, $R_c$, $R_d$, $R_e$, $R_f$, $R_g$, $R_h$ and $R_i$, are independently selected from hydrogen, $C_1$-$C_6$ alkyl, aryl, heterocyclyl, heteroaryl and trifluoromethyl.

The term "hydroxyl protecting group" (HPG) refers to a group blocking the OH function for subsequent reactions that can be removed under controlled conditions. Hydroxyl protecting groups are well known in the art. Illustrative examples of hydroxyl protecting groups have been described by Green T W et al. in "Protective Groups in Organic Synthesis", 3rd Edition (1999), Ed. John Wiley & Sons (ISBN 0-471-16019-9). Virtually any hydroxyl protecting group can be used to put the invention into practice. Illustrative, non-limiting examples of HPGs include:

silyl ethers [—Si(R)(R')(R")]. R, R' and R" can be independently selected from $C_1$-$C_6$ alkyl, $C_3$-$C_7$ cycloalkyl, $C_6$-$C_{14}$ aryl, $C_1$-$C_6$ alkoxy and halogen. Examples of silyl ethers include trimethylsilyl ether, triethylsilyl ether, tert-butyldimethylsilyl ether, tert-butyldiphenylsilyl ether, tri-isopropylsilyl ether, diethylisopropylsilyl ether, thexyldimethylsilyl ether, triphenylsilyl ether, di-tert-butylmethylsilyl ether;

ethers [—R]. R can be selected from $C_1$-$C_6$ alkyl, aryl and arylalkyl. Examples of ethers include methyl ether, tert-butyl ether, benzyl ether, p-methoxybenzyl ether, 3,4-dimethoxybenzyl ether, trityl ether, allyl ether;

alkoxy and aryloxy methyl ether [–$CH_2$—OR]. R can be selected from $C_1$-$C_6$ alkyl, aryl and arylakyl. Examples of alkoxy and aryloxy methyl ethers include methoxymethyl ether, 2-methoxyethoxymethyl ether, benzyloxymethyl ether, p-methoxybenzyloxymethyl ether, 2-(trimethylsilyl)ethoxymethyl ether; tetrahydropyranyl and related ethers;

esters [–COR]. R can be selected from $C_1$-$C_6$ alkyl, aryl and arylakyl. Examples of esters include acetate ester, benzoate ester, pivalate ester, methoxyacetate ester, chloroacetate ester, levulinate ester; and carbonates [–COOR]. R can be selected from $C_1$-$C_6$ alkyl, aryl and arylakyl. Examples of carbonates include benzyl carbonate, p-nitrobenzyl carbonate, tert-butyl carbonate, 2,2,2-trichloroethyl carbonate, 2-(trimethylsilyl)ethyl carbonate, allyl carbonate.

The invention also provides "salts" of the compounds described in the present description. By way of illustration, said salts can be acid addition salts, base addition salts or metal salts, and can be synthesized from the parent compounds containing a basic or acid moiety by means of conventional chemical processes known by the persons skilled in the art. Such salts are generally prepared, for example, by reacting the free acid or base forms of said compounds with a stoichiometric amount of the suitable base or acid in water or in an organic solvent or in a mixture of the two. Non-aqueous media such as ether, ethyl acetate, ethanol, acetone, isopropanol or acetonitrile are generally preferred. Illustrative examples of said acid addition salts include inorganic acid addition salts such as, for example, hydrochloride, hydrobromide, hydroiodide, sulfate, nitrate, phosphate, etc., organic acid addition salts such as, for example, acetate, maleate, fumarate, citrate, oxalate, succinate, tartrate, malate, mandelate, methanesulfonate, p-toluenesulfonate, camphorsulfonate, etc. Illustrative examples of base addition salts include inorganic base salts such as, for example, ammonium salts and organic base salts such as, for example, ethylenediamine, ethanolamine, N,N-dialkylenethanolamine, triethanolamine, glutamine, amino acid basic salts, etc. Illustrative examples of metal salts include, for example, sodium, potassium, calcium, magnesium, aluminum and lithium salts. In a particular embodiment, the salt is an acid addition salt, such as hydrochloride, fumarate or oxalate salt, preferably it is the hydrochloride or fumarate salt, more preferably it is the hydrochloride salt.

Likewise, the compounds described in the present description can be obtained both as free compounds or as solvates (e.g., hydrates, alcoholates, etc.), both forms being included within the scope of the present invention. The solvation methods are generally known in the state of the art. Preferably, the solvate is a hydrate.

Compounds are stereoisomers when they are formed by the same atoms bound by the same sequence of bonds, but with different three-dimensional structures which are not interchangeable, such as for example, enantiomers or diastereoisomers.

Compounds of general formula (I), (IV), (V), (VII), (VIII) comprise at least one asymmetric center and can therefore give rise to enantiomers with the spatial configuration (R) or (S). All the individual enantiomers of said compounds as well as their mixtures are included within the scope of the present invention.

Likewise, depending on the substituents, the compounds of general formula (IV) can have more than one asymmetric center and can therefore give rise to diastereoisomers. All the individual diastereoisomers of said compounds as well as their mixtures are included within the scope of the present invention. The individual diastereoisomers can be separated by means of conventional techniques.

The term "chiral alcohol" refers to a hydroxyl compound comprising a chiral centre. Preferably, the hydroxyl group is attached directly to a chiral centre. Preferably, the enantiomeric purity of the chiral alcohol is at least 90% ee, more preferably at least 95% ee, at least 98% ee, at least 99% ee, especially at least 99.5% ee. In an embodiment, it is enantiopure. The chiral alcohol can be a primary, secondary or tertiary alcohol. In an embodiment, the chiral alcohol is a secondary alcohol. Illustrative examples of chiral alcohols include, for example, (+)-menthol, (−)-menthol, (+)-isomenthol, (+)-neomenthol, (+)-neoisomenthol, (−)-8-phenylmenthol, (−)-trans-2-methylcyclohexanol, (−)-trans-2-tertbutylcyclohexanol, (−)-trans-2-phenylcyclohexanol, (S)-1-octyn-3-ol, (R)-3-methyl-2-butanol, (R)-2-methyl-butanol, (S)-1-phenyl-1-butanol, (S)-1-phenyl-1-propanol, (1R,2R)-2-benzoylcyclohexanol, (S)-2-butanol, (S)-1-(4-pyridyl) ethanol, (+1,2-dicyclohexyl-1,2-ethanediol, (−)-isopinocampheol, cholesterol, (1S,2S,5R)-2-isopropyl-1,5-dimethylcyclohexanol, (+)-borneol, (−)-10-dicyclohexylsulfamoyl-D-isoborneol, (+)-fenchyl alcohol, (−)-benzenesulfonyl-N-(3,5-dimethylphenyl)amino-2-borneol and the corresponding enantiomers thereof. Preferably, the chiral alcohol is (+)-menthol or (−)-menthol.

The term "chiral group" as used herein refers to the residue of the chiral alcohol as defined above.

In an aspect, the invention refers to a process for preparing a compound of formula (I) or (I'), or a solvate or salt thereof,

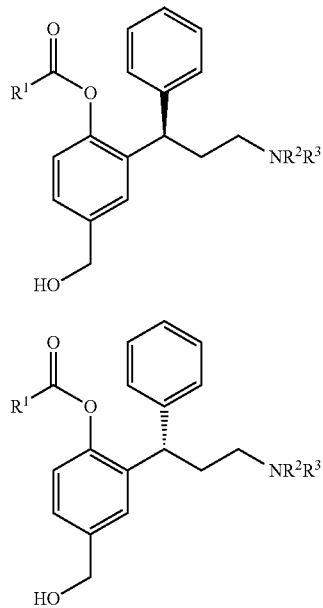

(I)

(I')

wherein
$R^1$ is $C_1$-$C_6$ alkyl; and
$R^2$ and $R^3$, independently of one another, are selected from H and $C_1$-$C_6$ alkyl, or
together form a ring of 3 to 7 members with the nitrogen to which they are bound; which comprises
(a) reacting a compound of formula (II), or a solvate or salt thereof,

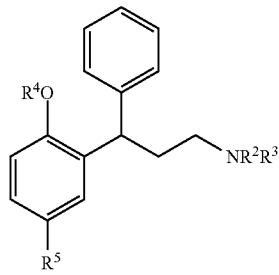

(II)

wherein
$R^4$ is hydrogen or a hydroxyl protecting group; and
$R^5$ is selected from —C(O)Cl, —C(O)Br, —C(O)OH, —C(O)OR', —C(O)OCOR' and CN,
wherein R' is selected from $C_1$-$C_6$ alkyl, $C_1$-$C_6$ haloalkyl, aryl and arylalkyl; with an optically active chiral alcohol (III)

$$R^6\text{—OH} \qquad (III)$$

wherein $R^6$ is a chiral group;
to yield compounds of formula (IV) and (IV'), or a solvate or salt thereof,

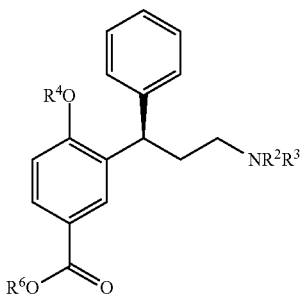

(IV)

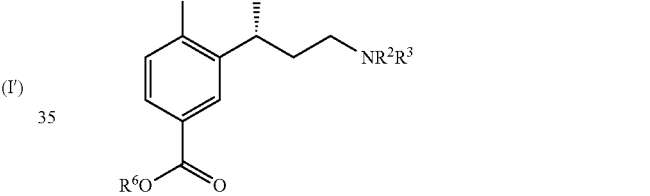

(IV')

wherein $R^2$, $R^3$, $R^4$ and $R^6$ are as defined previously;
(b) separating the compound of formula (IV) or (IV'), or a solvate or salt thereof; and
(c) converting the compound of formula (IV) or (IV'), or a solvate or salt thereof, into a compound of formula (I) or (I'), respectively, or a solvate or salt thereof.

Preferably, the invention refers to a process for obtaining a compound of formula (I) through ester (IV), as defined above.

In an embodiment, compound of formula (I) is Fesoterodine or a salt or solvate thereof.

In a preferred embodiment, compound of formula (I) is Fesoterodine.

In another preferred embodiment, compound of formula (I) is Fesoterodine hydrochloride or a solvate thereof, such as Fesoterodine hydrochloride monohydrate.

In another preferred embodiment, compound of formula (I) is Fesoterodine fumarate.

In a particular embodiment, the chiral alcohol of formula (III) is a compound wherein the hydroxyl group is attached directly to a chiral centre. Preferably, it is a chiral secondary alcohol wherein the hydroxyl group is attached directly to a chiral centre. In a particular embodiment, the chiral alcohol of formula (III) is selected from the group consisting of (+)-menthol, (−)-menthol, (+)-isomenthol, (+)-neoisomenthol, (−)-8-phenylmenthol, (−)-trans-2-methylcyclohexanol, (−)-trans-2-tertbutylcyclohexanol, (−)-trans-2-phenylcyclohexanol, (S)-1-octyn-3-ol, (R)-3- methyl-2-butanol, (R)-2-methyl-butanol, (S)-1-phenyl-1-butanol, (S)-1-phenyl-1-propanol, (1R,2R)-2-benzoylcyclohexanol, (S)-2-butanol, (S)-1-(4-pyridyl)ethanol, (−)-1,2-dicyclohexyl-1,2-ethanediol, (−)-isopinocampheol, cholesterol, (1S,2S,5R)-2-isopropyl-1,5-dimethylcyclohexanol, (+)-borneol, (+10-dicyclohexylsulfamoyl-D-isoborneol, (+)-fenchyl alcohol, (−)-benzenesulfonyl-N-(3,5-dimethylphenyl)amino-2-borneol and the corresponding enantiomers thereof. Preferably, it is selected from (+)-menthol, (−)-menthol and (S)-1-phenylethanol. More preferably, it is (+)-menthol.

$R^6$ is the residue of the chiral alcohol as defined herein.

In a particular embodiment, $R^1$ is $C_1$-$C_3$ alkyl, preferably it is isopropyl.

$R^2$ and $R^3$, independently of one another, are selected from H and $C_1$-$C_6$ alkyl, or together form a ring of 3 to 7 members with the nitrogen to which they are bound such as pyrrolidine, piperidine, piperazine, morpholine or azepane. In a particular embodiment, $R^2$ and $R^3$ are independently selected from $C_1$-$C_6$ alkyl. Preferably $R^2$ and $R^3$ are independently selected from $C_1$-$C_3$ alkyl, more preferably $R^2$ and $R^3$ are isopropyl.

In a particular embodiment, $R^4$ is hydrogen or a hydroxyl protecting group selected from a silyl ether, an alkyl-aryl- or arylalkylether, an alkoxy or aryloxy methyl ether, an ester and a carbonate. Preferably, $R^4$ is hydrogen.

In a particular embodiment, $R^5$ is selected from —C(O)Cl, —C(O)Br, —C(O)OH, —C(O)OR', —C(O)OCOR' and CN, wherein R' is selected from $C_1$-$C_3$ alkyl, $C_1$-$C_3$ haloalkyl, $C_6$-$C_{10}$ aryl and $(C_6$-$C_{10})$aryl($C_1$-$C_3$)alkyl. In another embodiment, $R^5$ is selected from —C(O)Cl, —C(O)Br, —C(O)OH, —C(O)OR', —C(O)OCOR' and CN, wherein R' is selected from methyl, ethyl, $CF_3$, phenyl and benzyl. Preferably, $R^5$ is selected from —C(O)Cl, —C(O)Br and —C(O)OH, more preferably $R^5$ is selected from —C(O)Cl and —C(O)Br, even more preferably $R^5$ is —C(O)Cl.

Obtaining Compounds of Formula (IV) and (IV')

The reaction of a compound of formula (II), or a salt or solvate thereof, with a chiral alcohol of formula (III) can be performed in the presence of an organic solvent, such as a cyclic or acyclic ether (e.g. $Et_2O$, $iPr_2O$, 1,4-dioxane, tetrahydrofuran, methyltetrahydrofuran, dimethoxyethane), a hydrocarbonated solvent (e.g. pentane, hexane, heptane), a halogenated solvent (e.g. dichloromethane, chloroform), an aromatic solvent (e.g. toluene, chlorotoluene, dichlorotoluene), a ketone (e.g. acetone), an ester (e.g. EtOAc, AcOiPr), a nitrile (e.g. acetonitrile, propionitrile), an alcohol (e.g. methanol, ethanol, isopropanol), an amide (DMF) or mixtures thereof. In a particular embodiment, it is performed in a solvent selected from acetonitrile, tetrahydrofuran, EtOAc, dichloromethane and mixtures thereof. Preferably, the reaction is performed in dichloromethane.

In a particular embodiment, the reaction of a compound of formula (II), or a salt or solvate thereof, with a chiral alcohol of formula (III) can be carried out at a temperature between 0° C. and the reflux temperature of the solvent; preferably, between 0 and 60° C.; more preferably, between 15 and 30° C.

In a particular embodiment, the reaction of a compound of formula (II), or a salt or solvate thereof, with a chiral alcohol is carried out using between 1 and 10, preferably between 1 and 5, more preferably between 1 and 2 equivalents of compound of formula (III) per equivalent of compound of formula (II).

The reaction of a compound of formula (II), or a salt or solvate thereof, with a chiral alcohol of formula (III) can be carried out in the presence of a base, in the presence of an acid or in the absence of both.

In an embodiment, the reaction of a compound of formula (II), or a salt or solvate thereof, with a chiral alcohol of formula (III) can be performed in the presence of a base. Suitable bases include organic bases, such as alkyl- or aromatic amines, preferably tertiary alkyl- or aromatic amines (e.g. $Et_3N$, DIPEA, pyridine), and inorganic bases, such as alkaline or alkaline earth metal carbonates or bicarbonates.

In a particular embodiment, the reaction of a compound of formula (II), or a salt or solvate thereof, with a chiral alcohol is carried out in the presence of a base using between 1 and 10, preferably between 1 and 5, more preferably between 1 and 3 equivalents of base per equivalent of compound of formula (II).

In an embodiment, the reaction of a compound of formula (II), or a salt or solvate thereof, with a chiral alcohol of formula (III) can be performed in the presence of an acid, such as an organic acid, an inorganic acid or a Lewis acid.

Diastereomeric esters of formula (IV) and (IV'), or salts or solvates thereof, can be separated by conventional methods known by the skilled in the art, for example, by crystallization, chromatographic methods, etc.

In an embodiment, the compound of formula (IV) or (IV'), or a salt or solvate thereof, is separated by chromatography.

In a particular embodiment, the compound of formula (IV) or (IV'), or a salt or solvate thereof, is separated by crystallization. In a particular embodiment, the compound of formula (IV) or (IV'), or a salt or solvate thereof, is separated by crystallization in an organic solvent, preferably in an organic solvent selected from acetone, isopropanol, acetonitrile, ethyl acetate, heptane and mixtures thereof; more preferably in acetone.

In an embodiment, the reaction of a compound of formula (II), or a salt or solvate thereof, with the chiral alcohol of formula (III) is performed in a solvent in which one of the compounds of formula (IV) or (IV'), or a salt or solvate thereof, is insoluble so that it directly precipitates and can be separated from the other diastereoisomer, e.g. by filtration. Even if one of the compounds of formula (IV) and (IV'), or a salt or solvate thereof, directly precipitates after its formation, the mixture of diastereoisomers can be also crystallized, e.g. by heating and then allowing it to cool, in order to improve the purity and/or yield of the desired product.

Alternatively, the reaction solvent can be changed afterwards to another solvent in which one of the compounds of formula (IV) or (IV'), or a salt or solvate thereof, is insoluble so that it precipitates and can be separated from the other diastereoisomer.

After crystallization, the compound of formula (IV) or (IV'), or a salt or solvate thereof, can be separated by conventional means, e.g. by filtration.

If the desired diastereomer is dissolved in the mother liquor, it can be obtained by conventional means, e.g. by crystallization in a suitable solvent or by chromatographic methods.

In an embodiment, compounds of formula (IV) and (IV') are in the form of a salt, preferably an acid addition salt such as hydrochloride salt or oxalate salt, more preferably hydrochloride salt.

In a particular embodiment, compounds of formula (IV) and (IV') are separated by crystallization in the form of a salt, preferably an acid addition salt such as hydrochloride salt or oxalate salt, more preferably hydrochloride salt.

Acid addition salts of a compound of formula (IV) or (IV') can be obtained directly by reacting the acid addition salt of a compound of formula (II) with a chiral alcohol of formula (III) as defined above. Acid addition salts of a compound of formula (IV) or (IV') can be also obtained by reacting a compound of formula (II) with a chiral alcohol of formula (III) in the presence of the corresponding acid. Alternatively, acid addition salts of a compound of formula (IV) or (IV') can be obtained by treating a compound of formula (IV) or (IV') with the corresponding acid.

In a particular embodiment, compounds of formula (IV) and (IV') are obtained in the form of an acid addition salt such as hydrochloride salt or oxalate salt, more preferably hydrochloride salt, by reacting the corresponding acid addition salt of a compound of formula (II) with a chiral alcohol of formula (III) in the absence of a base.

In another embodiment, compounds of formula (IV) and (IV') are obtained in the form of an acid addition salt such as hydrochloride salt or oxalate salt, more preferably hydrochloride salt, by reacting a compound of formula (II) with a chiral alcohol of formula (III) in the presence of the corresponding acid.

In another embodiment, compounds of formula (IV) and (IV') are obtained in the form of an acid addition salt such as hydrochloride salt or oxalate salt, more preferably hydrochloride salt, by reacting a compound of formula (II) with a chiral alcohol of formula (III) and treating the resulting compounds of formula (IV) and (IV') with the corresponding acid.

In another embodiment, compounds of formula (IV) and (IV') are obtained in the form of an acid addition salt such as hydrochloride salt or oxalate salt, more preferably hydrochloride salt, by reacting an acid addition salt such as hydrochloride salt or oxalate salt, more preferably hydrochloride salt, of a compound of formula (II) with a chiral alcohol of formula (III) in the presence of a base and treating the resulting compounds of formula (IV) and (IV') with the corresponding acid.

In a particular embodiment, compounds of formula (IV) and (IV') are obtained in the form of an acid addition salt such as hydrochloride salt or oxalate salt, more preferably hydrochloride salt, by:
(a) reacting the corresponding acid addition salt such as hydrochloride salt or oxalate salt, more preferably hydrochloride salt, of a compound of formula (II) with a chiral alcohol of formula (III) in the absence of a base, or
(b) reacting an acid addition salt such as hydrochloride salt or oxalate salt, more preferably hydrochloride salt, of a compound of formula (II) with a chiral alcohol of formula (III) in the presence of a base and treating the resulting compounds of formula (IV) and (IV') with the corresponding acid, such as hydrochloric acid or oxalic acid, more preferably hydrochloric acid.

Preferably, compounds of formula (IV) and (IV') in the form of an acid addition salt such as hydrochloride salt or oxalate salt, more preferably hydrochloride salt, are separated by crystallization.

In an embodiment, formation of the acid addition salts such as hydrochloride salts or oxalate salts, more preferably hydrochloride salts, of the compounds of formula (IV) or (IV') is performed in a solvent in which one of the diastereomeric salts is insoluble so that it directly precipitates and can be separated from the other diastereoisomer, e.g. by filtration. Even if one of the acid addition salts such as hydrochloride salts or oxalate salts, more preferably hydrochloride salts, of the compound of formula (IV) or (IV') directly precipitates after its formation, the mixture of diastereoisomers can be also crystallized, e.g. by heating and then allowing it to cool, in order to improve the purity and/or yield of the desired product.

Alternatively, after salt formation the solvent can be changed to another solvent in which one of the acid addition salts such as hydrochloride salts or oxalate salts, more preferably hydrochloride salts, of the compound of formula (IV) or (IV') is insoluble so that it precipitates and can be separated from the other diastereoisomer, e.g. by filtration.

In a particular embodiment, the compounds of formula (IV) and (IV') in the form of an acid addition salt such as hydrochloride salt or oxalate salt, more preferably hydrochloride salt, are separated by crystallization in an organic solvent selected from acetone, isopropanol, acetonitrile, ethyl acetate, heptane and mixtures thereof, preferably in acetone.

After crystallization, the acid addition salt such as hydrochloride salt or oxalate salt, more preferably hydrochloride salt, of the compound of formula (IV) or (IV'), can be separated by conventional means, e.g. by filtration.

If the desired diastereoisomer is dissolved in the mother liquor, it can be obtained by conventional means, e.g. by crystallization in a suitable solvent or by chromatographic methods.

In a particular embodiment, an acid addition salt such as hydrochloride salt or oxalate salt, more preferably hydrochloride salt, of a compound of formula (II) is reacted with a chiral alcohol of formula (III) to yield the corresponding acid addition salts of compounds of formula (IV) and (IV'), one of which is separated by crystallization in an organic solvent such as acetone, isopropanol, acetonitrile, ethyl acetate, heptane and mixtures thereof, preferably in acetone, and then converted into a compound of formula (I) or (I'), or a solvate or salt thereof.

In another embodiment, an acid addition salt such as hydrochloride salt or oxalate salt, more preferably hydrochloride salt, of a compound of formula (II) is reacted with a chiral alcohol of formula (III) in the presence of a base, the resulting compounds of formula (IV) and (IV') are treated with an acid, such as hydrochloric acid or oxalic acid, more preferably hydrochloric acid, to yield the corresponding acid addition salts of compounds of formula (IV) and (IV'), one of which is separated by crystallization in an organic solvent such as acetone, isopropanol, acetonitrile, ethyl acetate, heptane and mixtures thereof, preferably in acetone, and then converted into a compound of formula (I) or (I'), or a solvate or salt thereof.

In another aspect, the invention is directed to a compound of formula (IV) or (IV'), or a salt or solvate thereof, as defined herein.

Preferred compounds of formula (IV) and (IV') are those wherein $R^4$ is hydrogen and $R^2$ and $R^3$ are isopropyl (compounds IVa and IVa'). Preferably, $R^4$ is hydrogen, $R^2$ and $R^3$ are isopropyl and $R^6$ is the residue of (+)-menthol, (−)-menthol or (S)-1-phenylethanol, more preferably $R^6$ is the residue of (+)-menthol.

In a particular embodiment, the invention refers to an acid addition salt such as hydrochloride salt or oxalate salt, more preferably hydrochloride salt, of a compound of formula (IV) or (IV').

In another embodiment, the invention refers to a hydrochloride salt or oxalate salt of a compound of formula (IV) or (IV'), wherein $R^4$ is hydrogen, $R^2$ and $R^3$ are isopropyl and $R^6$ is the residue of (+)-menthol, (−)-menthol or (S)-1-phenylethanol, more preferably $R^6$ is the residue of (+)-menthol.

In a particular embodiment, the invention refers to a compound of formula (IV) or (IV') selected from:
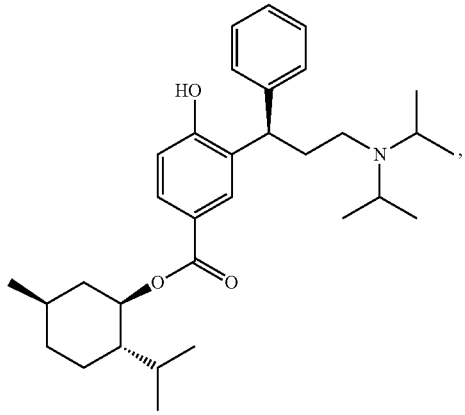
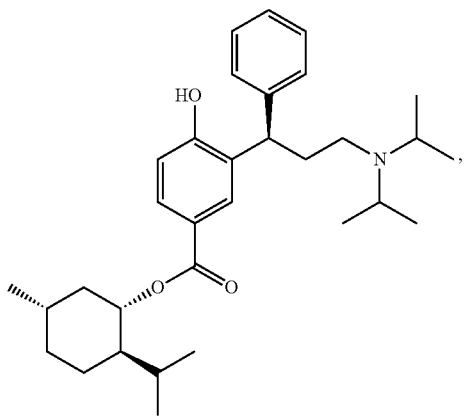
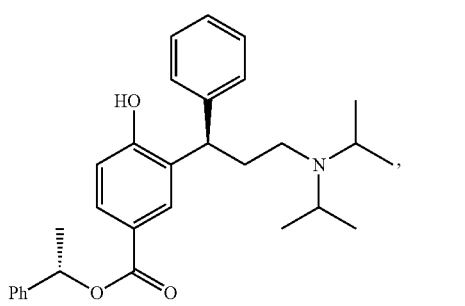
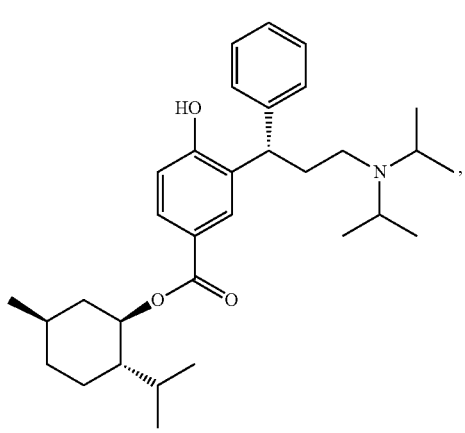
-continued
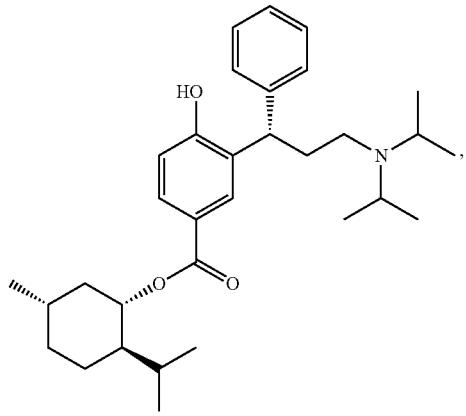
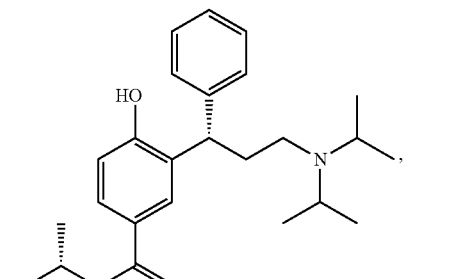
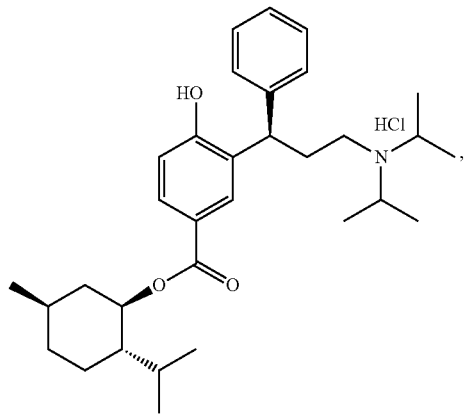
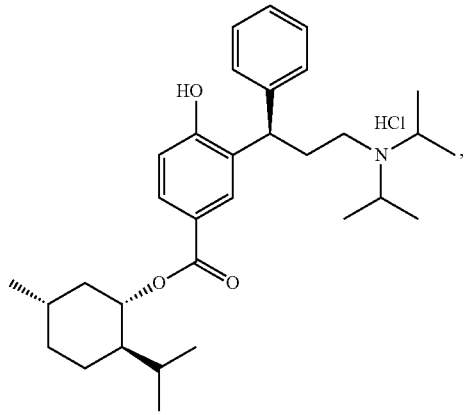

-continued

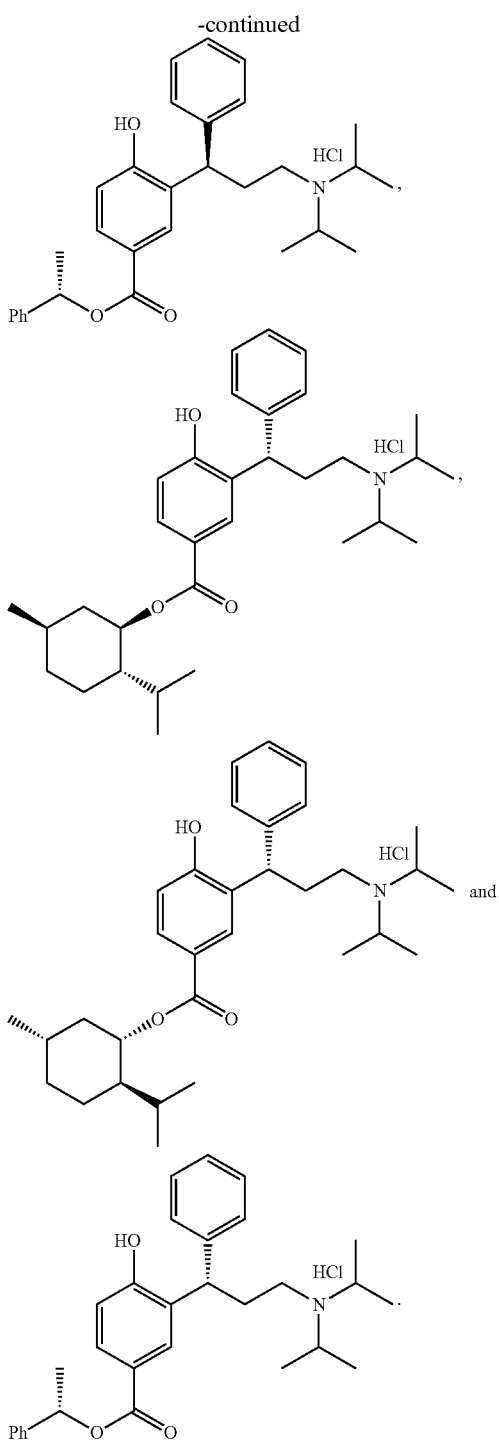

or a solvate thereof.

Compounds of Formula (II)

In a particular embodiment, $R^5$ is selected from —C(O)Cl, —C(O)Br and —C(O)OH, more preferably $R^5$ is selected from —C(O)Cl and —C(O)Br, even more preferably $R^5$ is —C(O)Cl.

In a particular embodiment, compound of formula (II) is in the form of a salt, preferably an acid addition salt such as hydrochloride salt or oxalate salt, more preferably hydrochloride salt.

In a particular embodiment, $R^5$ is —C(O)Cl and the compound of formula (II) is in the form of a hydrochloride salt.

In a particular embodiment, $R^5$ is —C(O)Cl, $R^4$ is hydrogen and $R^2$ and $R^3$ are isopropyl.

In an aspect, the invention is directed to a compound of formula (IIa)

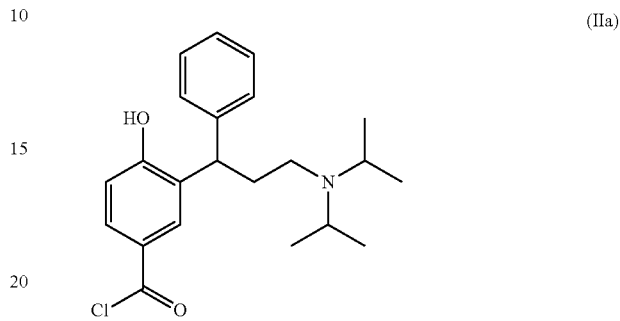

(IIa)

or salt or solvate thereof.

In a particular embodiment, the invention is directed to an acid addition salt such as hydrochloride or oxalate salt, preferably hydrochloride salt, of a compound of formula (IIa). Preferably, it is the hydrochloride salt of compound (IIa).

Compounds of formula (II) are known in the art or can be obtained by conventional methods.

In a particular embodiment, compound of formula (II) wherein $R^5$ is —C(O)Cl, or a salt or solvate thereof, is obtained by treating a compound of formula (II) wherein $R^5$ is —C(O)OH, or a salt or solvate thereof, with a chlorinating agent.

Suitable chlorinating agents include, for example, $SOCl_2$, $PCl_3$, $PCl_5$, $POCl_3$, $(CO)_2Cl_2$. In a particular embodiment, the chlorinating agent is $SOCl_2$.

In a particular embodiment, the compound of formula (II) wherein $R^5$ is —C(O)Cl, or a salt or solvate thereof, obtained by treating a compound of formula (II) wherein $R^5$ is —C(O)OH, or a salt or solvate thereof, with a chlorinating agent is directly reacted, without prior isolation (one-pot process), with the chiral alcohol of formula (III). In another embodiment, it is isolated prior to the reaction with the chiral alcohol of formula (III).

In an embodiment, hydrochloride salt of a compound of formula (II) wherein $R^5$ is —C(O)Cl, is obtained by treating a compound of formula (II) wherein $R^5$ is —C(O)OH with $SOCl_2$, and can be directly reacted, without prior isolation, with the chiral alcohol of formula (III) or can be isolated prior to the reaction with the chiral alcohol of formula (III).

The chlorination reaction can be performed in the presence of an organic solvent, such as a cyclic or acyclic ether (e.g. $Et_2O$, $iPr_2O$, 1,4-dioxane, tetrahydrofuran, methyltetrahydrofuran, dimethoxyethane), a hydrocarbonated solvent (e.g. pentane, hexane, heptane), a halogenated solvent (e.g. dichloromethane, chloroform), an aromatic solvent (e.g. toluene, chlorotoluene, dichlorotoluene), a ketone (e.g. acetone), an ester (e.g. EtOAc, AcOiPr), a nitrile (e.g. acetonitrile, propionitrile), an amide (DMF) or mixtures thereof. In a particular embodiment, it is performed in a solvent selected from acetonitrile, tetrahydrofuran, EtOAc, dichloromethane and mixtures thereof. Preferably, the reaction is performed in dichloromethane.

In a particular embodiment, the chlorination reaction can be carried out at a temperature between 0° C. and the reflux temperature of the solvent; preferably, between 0 and 60° C.; more preferably, between 15 and 30° C.

In a particular embodiment, the chlorination reaction is carried out using between 1 and 10, preferably between 1 and 6, more preferably between 1 and 2 equivalents of chlorinating agent per equivalent of compound of formula (II) wherein $R^5$ is —C(O)OH.

The chlorination reaction can be carried out in the presence of a catalyst. In a particular embodiment, the chlorination reaction is carried out in the presence of a catalyst selected from DMF and pyridine, preferably DMF.

Obtaining Compounds of Formula (I)

Compounds of formula (IV) or (IV'), or salts or solvates thereof as defined above, can be converted respectively into a compound of formula (I) or (I'), or a salt or solvate thereof, by conventional methods known by those skilled in the art (e.g. U.S. Pat. No. 6,858,650, U.S. Pat. No. 7,384,980, EP 2338871, EP 2281801).

In a particular embodiment, the compound of formula (IV) or (IV'), or a salt or solvate thereof as defined above, is transformed into a compound of formula (I) or (I'), or a salt or solvate thereof, by a process comprising:

(a) subjecting compound of formula (IV), or (IV'), or a salt or solvate thereof, to a reduction reaction to obtain, respectively, a compound of formula (V) or (V'), or a salt or solvate thereof,

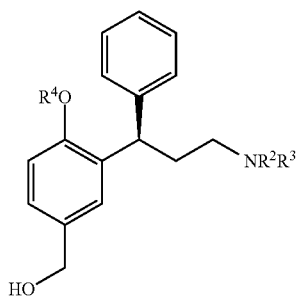

(V)

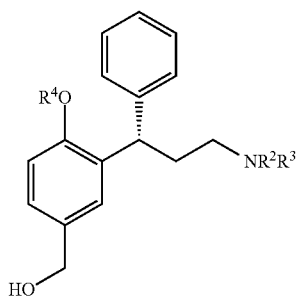

(V')

wherein $R^2$, $R^3$ and $R^4$ are as defined herein;

(b) if $R^4$ is a hydroxyl protecting group, deprotecting it either before or after step (a); and (c) subjecting compound of formula (V) or (V'), or a salt or solvate thereof, wherein $R^4$ is hydrogen to an esterification reaction with a compound of formula (VI)

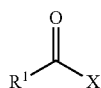

(VI)

wherein $R^1$ is as defined herein, and

X is selected from Cl, Br, OH, OR" and OCOR", wherein R" is selected from $C_1$-$C_6$ alkyl, $C_1$-$C_6$ haloalkyl, aryl and arylalkyl.

Deprotection conditions of a hydroxyl protecting group are well known in the art (e.g. Green T W et al. in "Protective Groups in Organic Synthesis", 3rd Edition (1999), Ed. John Wiley & Sons) or can be determined by the skilled in the art in view of the nature of the $R^4$ group.

Reduction reaction in step (a) can be carried out under conventional conditions known in the art. In a particular embodiment, the reaction is performed using a reducing agent selected from lithium borohydride, lithium triethylborohydride, lithium aluminium hydride and sodium bis(2-methoxyethoxy)aluminiumhydride (Red-Al or vitride). In a particular embodiment, the reducing agent is selected from lithium aluminium hydride and sodium bis(2-methoxyethoxy)aluminiumhydride (Red-Al).

The reduction reaction can be performed in the presence of an organic solvent, such as a cyclic or acyclic ether (e.g. $Et_2O$, $iPr_2O$, 1,4-dioxane, tetrahydrofuran, methyltetrahydrofuran, dimethoxyethane), a hydrocarbonated solvent (e.g. pentane, hexane, heptane), an aromatic solvent (such as toluene, xylene), or mixtures thereof. In a particular embodiment, it is performed in tetrahydrofuran or toluene.

In a particular embodiment, the reduction reaction is carried out using between 1 and 10, preferably between 1 and 5, more preferably between 1 and 3 equivalents of the reducing agent per equivalent of compound of formula (IV) or (IV'), or a salt or solvate thereof.

The compound of formula (V) or (V'), or a salt or solvate thereof, wherein $R^4$ is hydrogen can be esterified with a compound of formula (VI) under conventional conditions known in the art.

In a particular embodiment, $R^1$ is $C_1$-$C_3$ alkyl, preferably it is isopropyl.

In a particular embodiment, X is selected from Cl and Br, preferably Cl.

In a preferred embodiment, compound of formula (VI) is isobutyryl chloride.

The esterification can be carried out in the presence of a base, such as triethylamine, diisopropylethylamine, pyridine, sodium hydroxide, etc. The reaction can be performed in an organic solvent such as a halogenated hydrocarbon (e.g. dichloromethane, etc.), an ether (e.g. $Et_2O$, $iPr_2O$, 1,4-dioxane, tetrahydrofuran, methyltetrahydrofuran, dimethoxyethane, etc.), an aromatic hydrocarbon (e.g. toluene, etc.), etc.

In a particular embodiment, the compound of formula (IV) or (IV'), or a salt or solvate thereof as defined above, is transformed into a compound of formula (I) or (I'), or a salt or solvate thereof, by a process comprising:

(a) subjecting compound of formula (IV), or (IV'), or a salt or solvate thereof, to a hydrolysis reaction to obtain, respectively, a compound of formula (VII) or (VII'), or a salt or solvate thereof, (VII)

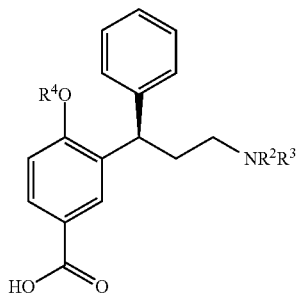

(VII')

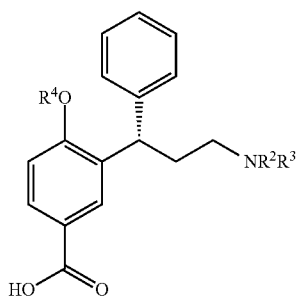

wherein $R^2$, $R^3$ and $R^4$ are as defined herein;
(b) if $R^4$ is a hydroxyl protecting group, deprotecting it either before or after step (a);
(c) subjecting compound of formula (VII) or (VII'), or a salt or solvate thereof, wherein $R^4$ is hydrogen, to an esterification reaction with a compound of formula (VI)

(VI)

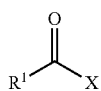

wherein
$R^1$ is as defined herein, and
X is selected from Cl, Br, OH, OR" and OCOR", wherein R" is selected from $C_1$-$C_6$ alkyl, $C_1$-$C_6$ haloalkyl, aryl and arylalkyl, to obtain a compound of formula (VIII) or (VIII'), or a salt or solvate thereof, (VIII)

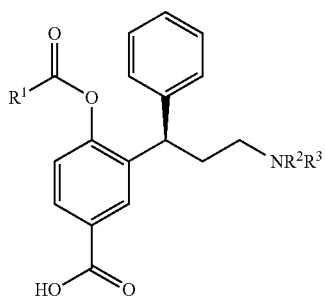

(VIII')

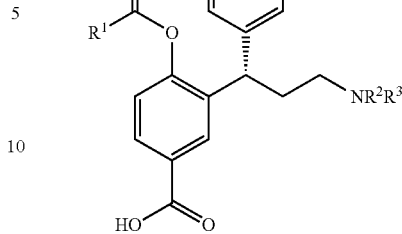

wherein $R^1$, $R^2$ and $R^3$ are as defined herein; and
(d) subjecting compound of formula (VIII), or (VIII'), or a salt or solvate thereof, to a chemoselective reduction.

Deprotection conditions of a hydroxyl protecting group are well known in the art (e.g. Green T W et al. in "Protective Groups in Organic Synthesis", 3rd Edition (1999), Ed. John Wiley & Sons) or can be determined by the skilled in the art in view of the nature of the $R^4$ group.

Hydrolysis conditions of an ester to a carboxylic acid are known in the art. In an embodiment, hydrolysis reaction in step (a) can be carried out under basic or acid conditions.

Basic hydrolysis conditions include, by way of a non-limiting illustration, the use of bases such as NaOH, KOH, LiOH, CsOH, alkaline metal carbonates, etc. It can be carried out in an aqueous medium or in a medium comprising a water/solvent mixture, wherein the solvent can be an alcohol (e.g. MeOH, EtOH, iPrOH, nBuOH, a glycol, e.g. ethylene glycol, etc.), an ether (e.g. diethylether, dioxane, tetrahydrofuran etc), a ketone (acetone, methyl ethyl ketone), a sulfoxide (DMSO). In a particular embodiment, the hydrolysis reaction is performed using NaOH or KOH in a mixture of MeOH/water.

Acid hydrolysis conditions include, by way of a non-limiting illustration, the use of acids such as hydrochloric acid, sulfuric acid, etc. It can be carried out in an aqueous medium or in a medium comprising a water/solvent mixture, wherein the solvent can be an alcohol (e.g. MeOH, EtOH, iPrOH, nBu, a glycol, e.g. ethylene glycol, etc.), an ether (e.g. diethylether, dioxane, tetrahydrofuran etc), a ketone (acetone, methyl ethyl ketone).

Hydrolysis reaction can be performed at a temperature comprised between room temperature and the reflux temperature of the chosen solvent.

The compound of formula (VII) or (VII'), or a salt or solvate thereof, wherein $R^4$ is hydrogen can be esterified with a compound of formula (VI) under conventional conditions known in the art.

In a particular embodiment, $R^1$ is $C_1$-$C_3$ alkyl, preferably it is isopropyl.

In a particular embodiment, X is selected from Cl and Br, preferably Cl.

In a preferred embodiment, compound of formula (VI) is isobutyryl chloride.

The esterification can be carried out in the presence of a base, such as triethylamine, diisopropylethylamine, pyridine, sodium hydroxide etc. The reaction can be performed in an organic solvent such as a halogenated hydrocarbon (e.g. dichloromethane, etc.), an ether (e.g. $Et_2O$, $iPr_2O$, 1,4-dioxane, tetrahydrofuran, methyltetrahydrofuran, dimethoxyethane, etc.), an aromatic hydrocarbon (e.g. toluene, etc.), etc.

The compound of formula (VIII) or (VIII'), or a salt or solvate thereof, can be subjected to a chemoselective reduction to give rise, respectively, to a compound of general formula (I) or (I'), or a salt or solvate thereof, by means of the use of a reducing agent capable of preferably reducing the carboxyl (—COOH) over the ester (—COOR₁) group.

As used in this description, a reduction is chemoselective when the reducing agent preferably reduces the carboxyl group against the ester group. By way of illustration, the selectivity of the reducing agent towards the carboxyl group is equal to or greater than 80%, advantageously, equal to or greater than 85%, preferably, equal to or greater than 90%, more preferably, equal to or greater than 95%, even more preferably, equal to or greater than 96%, 97%, 98% or 99%.

This reduction reaction can be carried out using different reducing agents, including aluminum hydrides ($AlH_3$), or a borane, or derivatives or precursors thereof. Illustrative non-limiting examples of borane derivatives include diborane, pinacolborane, catecholborane, thexylborane, borane-tetrahydrofuran ($BH_3 \cdot THF$) complexes [N. M. Yoon, C. S. Pak, H. C. Brown, S. Krishnamurthy, and T. P. Stocky, J. Org. Chem., 38, 2786 (1973)], borane-dimethyl sulfide ($BH_3 \cdot Me_2S$) complexes [L. M. Braun, R. A. Braun, H. R. Crissman, M. Opperman, and R. M. Adams, J. Org. Chem., 36, 2388 (1971)], etc. Likewise, illustrative non-limiting examples of borane precursors include compounds which generate borane or diborane in the reaction medium, such as, for example, $NaBH_4/I_2$, $NaBH_4/BF_3(OEt)_2$, $NaBH_4/HCl$, etc., and, in short, any reducer which generates borane or diborane in the reaction medium.

In a particular embodiment, the chemoselective reduction is carried out in the presence of a borane, such as diborane, borane-dimethyl sulfide complex, borane-tetrahydrofuran complex, catecholborane or thexylborane.

The chemoselective reduction reaction can be carried out in a suitable solvent, such as a cyclic or acyclic ether (e.g. $Et_2O$, $iPr_2O$, 1,4-dioxane, tetrahydrofuran, methyltetrahydrofuran, dimethoxyethane), a hydrocarbonated solvent (e.g. pentane, hexane, heptane), an aromatic solvent (e.g. toluene), or mixtures thereof.

Said chemoselective reduction reaction can be carried out at a temperature comprised between −75° C. and the reflux temperature of the solvent.

In a particular embodiment the chemoselective reduction reaction is performed using borane-dimethyl sulfide complex, in THF at temperature of 0-30° C.

In a particular embodiment, compound of formula (I) or (I') is in the form of an acid addition salt, such as hydrochloride salt, fumarate salt, or a solvate thereof.

In an embodiment, said acid addition salts of a compound of formula (I) or (I') can be obtained from the parent compound of formula (I) or (I') by means of conventional processes known by the skilled in the art. Preferably, by reacting the free amine form of a compound of formula (I) or (I') with a suitable acid, e.g. hydrochloric acid or fumaric acid.

In a particular embodiment, the compound of formula (I) or (I') obtained according to the process of the invention is further converted into a salt thereof by treatment with an acid. In a preferred embodiment, the compound of formula (I) or (I') obtained according to the process of the invention is further converted into a hydrochloride salt or a solvate therefore, such as hydrochloride monohydrate, preferably by treatment with hydrochloric acid. In a preferred embodiment, the compound of formula (I) or (I') obtained according to the process of the invention is further converted into a fumarate salt, preferably by treatment with fumaric acid.

In an embodiment, the compound of formula (I) or (I') obtained according to the process of the invention is converted into the hydrochloride salt or a solvate thereof, such as hydrochloride monohydrate, which is then converted into the fumarate salt.

Obtaining Fesoterodine

In an embodiment, compound of formula (I) is Fesoterodine or a salt or solvate thereof.

In a particular embodiment, compound of formula (I) is Fesoterodine.

In another embodiment, compound of formula (I) is Fesoterodine hydrochloride or a solvate thereof, such as Fesoterodine hydrochloride monohydrate.

In another embodiment, compound of formula (I) is Fesoterodine fumarate.

In a particular embodiment, Fesoterodine, or an enantiomer, salt or solvate thereof, is obtained by a process comprising (a) reacting a compound of formula (IIa), or a salt or solvate thereof,

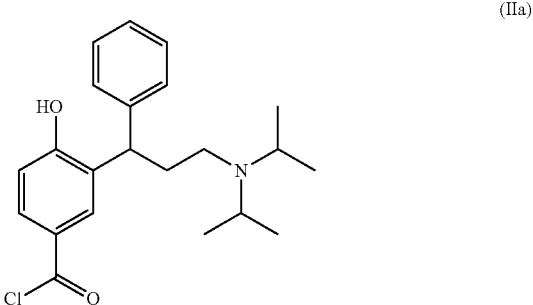 [SMILES: CC(C)N(CCC(c1ccccc1)c1cc(C(=O)Cl)ccc1O)C(C)C]

with an optically active chiral alcohol (III)

$R^6$—OH    (III)

wherein $R^6$ is as defined above;
to yield a compound of formula (IVa) and the diastereoisomer, or a salt or solvate thereof,

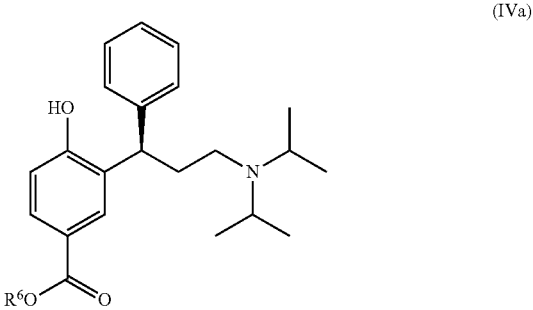

(b) separating the compound of formula (IVa) or the diastereoisomer, or a salt or solvate thereof; and
(c) converting the compound of formula (IVa) or the diastereoisomer, or a salt or solvate thereof, into Fesoterodine, or an enantiomer, salt or solvate thereof. Suitable reaction conditions and reagents are as defined above.

In a particular embodiment, the chiral alcohol of formula (III) is a compound wherein the hydroxyl group is attached directly to a chiral centre. Preferably, it is a chiral secondary alcohol wherein the hydroxyl group is attached directly to a chiral centre. In a particular embodiment, the chiral alcohol of formula (III) is selected from the group consisting of (+)-menthol, (−)-menthol, (+)-isomenthol, (+)-neomenthol, (+)-neoisomenthol, (+)-8-phenylmenthol, (−)-trans-2-methylcyclohexanol, (−)-trans-2-tertbutylcyclohexanol, (−)-trans-2-phenylcyclohexanol, (S)-1-octyn-3-ol, (R)-3-methyl-2-butanol, (R)-2-methyl-butanol, (S)-1-phenyl-1-butanol, (S)-1-phenyl-1-propanol, (1R,2R)-2-benzoylcyclohexanol, (S)-2-butanol, (S)-1-(4-pyridyl)ethanol, (−)-1,2-dicyclohexyl-1,2-ethanediol, (−)-isopinocampheol, cholesterol, (1S,2S,5R)-2-isopropyl-1,5-dimethylcyclohexanol, (+)-borneol, (−)-10-dicyclohexylsulfamoyl-D-isoborneol, (+)-fenchyl alcohol, (−)-benzenesulfonyl-N-(3,5-dimethylphenyl)amino-2-borneol and the corresponding enantiomers thereof. Preferably, it is selected from (+)-menthol, (−)-menthol and (S)-1-phenylethanol. More preferably, it is (+)-menthol.

In a particular embodiment, compound of formula (IIa) is in the form of an acid addition salt, such as hydrochloride salt or oxalate salt, preferably hydrochloride salt.

In a particular embodiment, the acid addition salt of a compound of formula (IIa) is reacted with a chiral alcohol of formula (III) in the absence of a base, to yield the acid addition salt of a compound of formula (IVa) and it's diastereoisomer, one of which is separated and then converted into Fesoterodine, or an enantiomer, salt or solvate thereof.

In another embodiment, the acid addition salt of a compound of formula (IIa) is reacted with a chiral alcohol of formula (III) in the presence of a base, to yield a compound of formula of formula (IVa) and the diastereoisomer, which are then reacted with an acid to yield the corresponding acid addition salt of a compound of formula (IVa) and of the diastereomer, one of which is separated and then converted into Fesoterodine, or an enantiomer, salt or solvate thereof.

In a particular embodiment, the hydrochloride or oxalate salt of compound (IIa), preferably the hydrochloride salt, is reacted with a chiral alcohol of formula (III) in the absence of a base, to yield the hydrochloride or oxalate salt of a compound of formula of formula (IVa) and of the diastereoisomer, preferably the hydrochloride salt, one of which is separated and then converted into Fesoterodine, or an enantiomer, salt or solvate thereof.

In a particular embodiment, the hydrochloride or oxalate salt of compound (IIa), preferably the hydrochloride salt, is reacted with a chiral alcohol of formula (III) in the presence of a base, to yield a compound of formula (IVa) and the diastereoisomer, which are then reacted with hydrochloric or oxalic acid to yield the hydrochloride or oxalate salt of a compound of formula (IVa) and of the diastereoisomer, preferably the hydrochloride salt, one of which is separated and then converted into Fesoterodine, or an enantiomer, salt or solvate thereof.

In a particular embodiment, the compound of formula (IIa), or a salt or solvate thereof, is obtained from the corresponding carboxylic acid by treatment with a chlorinating agent such as $SOCl_2$, $PCl_3$, $PCl_5$, $POCl_3$, $(CO)_2Cl_2$, preferably $SOCl_2$.

In a particular embodiment, hydrochloride salt of compound of formula (IIa) is obtained by treating the corresponding carboxylic acid with $SOCl_2$ and is then directly reacted, without prior isolation, with the chiral alcohol of formula (III).

In another embodiment, hydrochloride salt of compound of formula (IIa) is obtained by treating the corresponding carboxylic acid with $SOCl_2$ and is then isolated prior to the reaction with the chiral alcohol of formula (III).

In an embodiment, the acid addition salt of the compound of formula (IVa), such as hydrochloride or oxalate salt, preferably hydrochloride salt, or of the diastereomer, is separated by crystallization, preferably in an organic solvent selected from acetone, isopropanol, acetonitrile, ethyl acetate, heptanes and mixtures thereof, more preferably in acetone.

In a particular embodiment, compound of formula (IVa) or a diastereomer, or a salt or solvate thereof, can be then converted into Fesoterodine, or an enantiomer, solvate or salt thereof, by a process comprising:

(a) subjecting compound of formula (IVa) or a diastereoisomer, or a solvate or salt thereof, to a reduction reaction to obtain a compound of formula (Va), or an enantiomer, solvate or salt thereof,

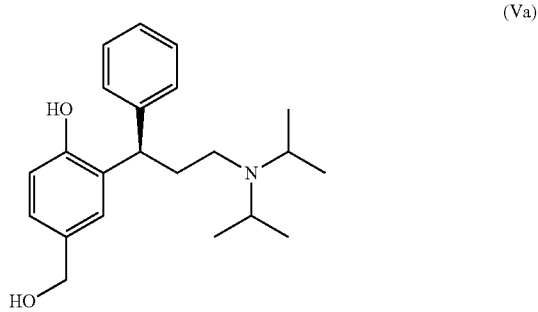 [SMILES: CC(C)N(CC[C@H](c1ccccc1)c1cc(CO)ccc1O)C(C)C]

(Va)

(b) subjecting compound of formula (Va), or an enantiomer, solvate or salt thereof, to an esterification reaction with a compound of formula (VIa)

(VIa)

wherein X is selected from Cl, Br, OH, OR" and OCOR", wherein R" is selected from $C_1$-$C_6$ alkyl, $C_1$-$C_6$ haloalkyl, aryl and arylalkyl.

Suitable reaction conditions and reagents are as defined above.

Preferably, X is Cl.

In a preferred embodiment, compound of formula (IVa) or a diastereoisomer thereof, is in the form of an acid addition salt such as hydrochloride or oxalate salt, preferably hydrochloride salt.

In a particular embodiment, an acid addition salt such as hydrochloride or oxalate salt, preferably hydrochloride salt, of a compound of formula (IVa) or of a diastereoisomer, is subjected to a reduction reaction using preferably lithium aluminium hydride or Red-Al, to yield compound of formula (Va), or an enantiomer, salt or solvate thereof, which is reacted with isobutyryl chloride to yield Fesoterodine, or an enantiomer, salt or solvate thereof.

In a particular embodiment, compound of formula (IVa) or a diastereomer, or a salt or solvate thereof, can be then converted into Fesoterodine, or an enantiomer, solvate or salt thereof, by a process comprising:

(a) subjecting compound of formula (IVa), or a diastereoisomer, solvate or salt thereof, to a hydrolysis reaction to obtain a compound of formula (VIIa), or an enantiomer, solvate or salt thereof,

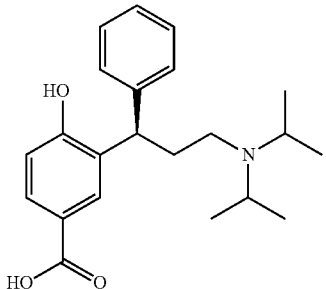

(VIIa)

(b) subjecting compound of formula (VIIa), or an enantiomer, solvate or salt thereof, to an esterification reaction with a compound of formula (VIa)

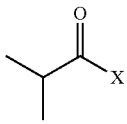

(VIa)

wherein X is selected from Cl, Br, OH, OR" and OCOR", wherein R" is selected from $C_1$-$C_6$ alkyl, $C_1$-$C_6$ haloalkyl, aryl and arylalkyl, to obtain a compound of formula (VIIIa), or an enantiomer, solvate or salt thereof,

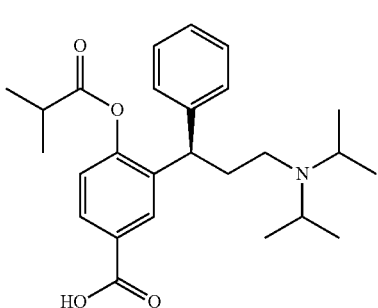

(VIIIa)

(c) subjecting compound of formula (VIIIa), or an enantiomer, solvate or salt thereof, to a chemoselective reduction.

Suitable reaction conditions and reagents are as defined above.

Preferably, X is Cl.

In a preferred embodiment, compound of formula (IVa), or a diastereoisomer thereof, is in the form of an acid addition salt such as hydrochloride or oxalate salt, preferably hydrochloride salt.

In a particular embodiment, an acid addition salt such as hydrochloride or oxalate salt, preferably hydrochloride salt, of a compound of formula (IVa), or of a diastereoisomer, is subjected to a hydrolysis reaction preferably under basic conditions, to yield compound of formula (VIIa), or an enantiomer, salt or solvate thereof, which is reacted with isobutyryl chloride to yield compound of formula (VIIIa), or an enantiomer, salt or solvate thereof, which is subjected to a chemoselective reduction, preferably, with a borane such as borane-DMS complex, to yield Fesoterodine, or an enantiomer, salt or solvate thereof.

In a particular embodiment, Fesoterodine is in the form of an acid addition salt, such as hydrochloride salt, fumarate salt, or a solvate thereof.

In a particular embodiment, Fesoterodine in the free amine form obtained according to the process of the invention is further converted into a salt thereof by treatment with an acid. In a preferred embodiment, Fesoterodine in the free amine form obtained according to the process of the invention is further converted into Fesoterodine hydrochloride or Fesoterodine hydrochloride monohydrate, preferably by treatment with hydrochloric acid. In a preferred embodiment, Fesoterodine in the free form obtained according to the process of the invention is further converted into Fesoterodine fumarate, preferably by treatment with fumaric acid.

In an embodiment, Fesoterodine obtained according to the process of the present invention is further converted into Fesoterodine hydrochloride or Fesoterodine hydrochloride monohydrate, which is converted into Fesoterodine fumarate.

The following examples illustrate the invention and must not be considered in a limiting sense thereof.

EXAMPLES

Example 1

Preparation of the D-(+)-menthyl 3-(3-N,N'-diisopropylamino-1(R)-phenyl-propyl)-4-hydroxy-benzoate hydrochloride

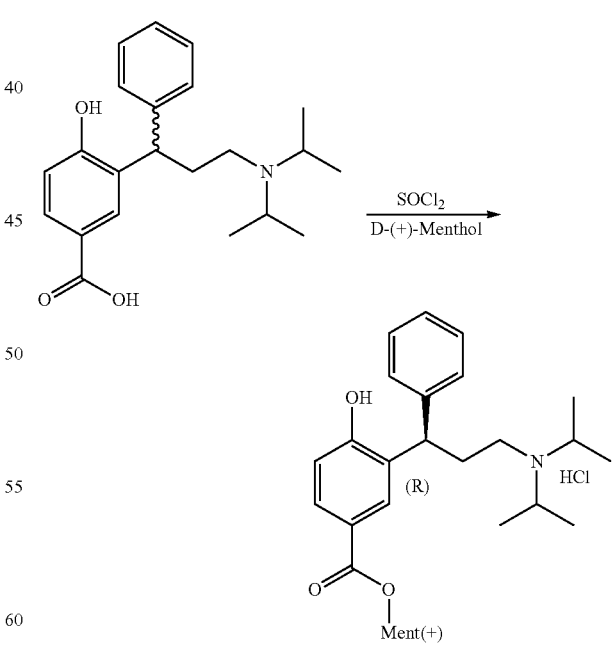

Alternative A

Racemic 3-(3-N,N'-diisopropylamino-1-phenyl-propyl)-4-hydroxy-benzoic acid (10 g, 28 mmol) was dissolved in 100 ml of dichloromethane under inert atmosphere, at a temperature of about 10-15° C. and 3 ml of thionyl chloride (41.3 mmol, 1.48 eq) and 0.1 eq of DMF were added thereto. The reaction mixture was stirred at room temperature for about one hour until completion of the reaction was observed by HPLC.

Then, D-(+)-menthol (7.84 g, 50 mmol, 1.79 eq) was added in portions and the mixture was stirred at room temperature for about 18 hours.

Water was added to obtain two phases, the separated organic phase was washed again with water and evaporated under reduced pressure and acetone was added. The suspended solid formed was cooled, filtered and washed with acetone to yield 5.2 g of the corresponding D-(+)-menthyl 3-(3-N,N'-diisopropylamino-1(R)-phenyl-propyl)-4-hydroxy-benzoate hydrochloride (35.0% yield) with a purity of about 100% by HPLC in relation with the other diastereoisomer (D-(+)-Menthyl 3-(3-N,N'-diisopropylamino-1(S)-phenyl-propyl)-4-hydroxy-benzoate hydrochloride remaining in the mother's liquor).

$^1$H NMR (400 MHz, CDCl$_3$) δ 7.77 (d, 1H), 7.63 (dd, 1H), 7.27 (m, 4H), 7.17 (m, 1H), 6.98 (d, 1H), 4.70 (m, 1H), 4.35 (t, 1H), 3.54 (m, 2H), 2.88 (m, 2H) 2.47 (m, 1H), 1.92 (m, 1H), 1.75 (m, 1H), 1.62 (m, 2H), 1.45 (m, 2H), 1.23 (dd, 6H), 1.16 (dd, 6H), 1.05 (m, 2H), 0.84 (dd, 6H), 0.67 (d, 3H).

Alternative B

Racemic 3-(3-N,N'-diisopropylamino-1-phenyl-propyl)-4-hydroxy-benzoic acid (6 g, 16.8 mmol) was dissolved in 60 ml of dichloromethane under inert atmosphere, at a temperature of about 10-15° C. and 5 ml of thionyl chloride (69 mmol, 4.1 eq) were added thereto together with a few drops of DMF as catalyst. The reaction mixture was stirred at room temperature for about one hour until completion of the reaction was observed by HPLC. The solvent and remaining thionyl chloride were evaporated under reduced pressure until residue.

The resulting residue (foam appearance) was redissolved in 60 ml of dichloromethane and D-(+)-menthol (3.92 g, 25 mmol, 1.48 eq) was added in portions followed by 4.7 ml of Et$_3$N (34 mmol, 2.02 eq). The mixture was stirred at room temperature for about 1 hour and water was added to obtain two phases. The organic phase was separated, washed with water and partially evaporated under reduced pressure.

Acetone (60 ml) was added, and the solvent was again partially evaporated under reduced pressure. This operation was repeated again to assure that all of the dichloromethane was eliminated.

A solution of chlorhydric acid in isopropanol (17 mmol) was added to form the chlorhydrate salt that precipitated. The suspended solid formed was cooled, filtered and washed with acetone to yield 1.55 g of the corresponding D-(+)-menthyl 3-(3-N,N'-diisopropylamino-1(R)-phenyl-propyl)-4-hydroxy-benzoate hydrochloride with a purity of about 100% by HPLC in relation with the other diastereoisomer (D-(+)-Menthyl 3-(3-N,N'-diisopropylamino-1(S)-phenyl-propyl)-4-hydroxy-benzoate hydrochloride remaining in the mother's liquor).

Alternative C

Racemic clorhydrate salt of 3-(3-N,N'-diisopropylamino-1-phenyl-propyl)-4-hydroxy-benzoil chloride previously formed (5 g, 12 mmol) was dissolved in 40 ml of dichloromethane under inert atmosphere at room temperature and 2.81 g of D-(+)-menthol (18 mmol, 1.5 eq) were added in portions. The mixture was stirred at room temperature for about 20 hours. The solvent was evaporated under reduced pressure and acetone was added.

The suspended solid formed was heated at 45° C. with stirring and then cooled, filtered and washed with acetone to yield 2 g of the corresponding D-(+)-menthyl 3-(3-N,N'-diisopropylamino-1(R)-phenyl-propyl)-4-hydroxy-benzoate hydrochloride (32% yield) with a purity of about 100% by HPLC in relation with the other diastereoisomer (D-(+)-menthyl 3-(3-N,N'-diisopropylamino-1(S)-phenyl-propyl)-4-hydroxy-benzoate hydrochloride remaining in the mother's liquor).

Example 2

Preparation of the Racemic Chlorhydrate Salt of 3-(3-N,N'-diisopropylamino-1-phenyl-propyl)-4-hydroxy-benzoil chloride

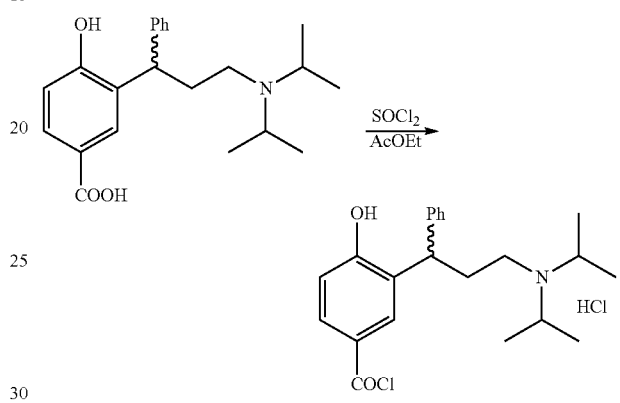

Thionyl chloride (6.5 ml, 90 mmol, 2 eq) and DMF (0.3 ml) were added to a suspension of racemic 3-(3-N,N'-diisopropylamino-1-phenyl-propyl)-4-hydroxy-benzoic acid (15 g, 42 mmol) in 100 ml of AcOEt. The resulting mixture was stirred for 2-4 h and then filtered, washed with more solvent and allowed to dry in a vacuum oven at room temperature. A solid (7.4 g) was obtained, which was directly used in the next step.

$^1$H NMR (400 MHz, CDCl$_3$) δ 9.81 (bs, 1H), 7.74 (s, 1H), 7.72 (d, 1H), 7.38 (d, 1H), 7.17 (m, 5H), 4.36 (t, 1H), 3.44 (bs, 2H), 2.85 (bs, 2H) 2.62 (bs, 2H), 1.20 (m, 12H).

Example 3

Preparation of the L-(−)-menthyl 3-(3-N,N'-diisopropylamino-1(S)-phenyl-propyl)-4-hydroxy-benzoate hydrochloride

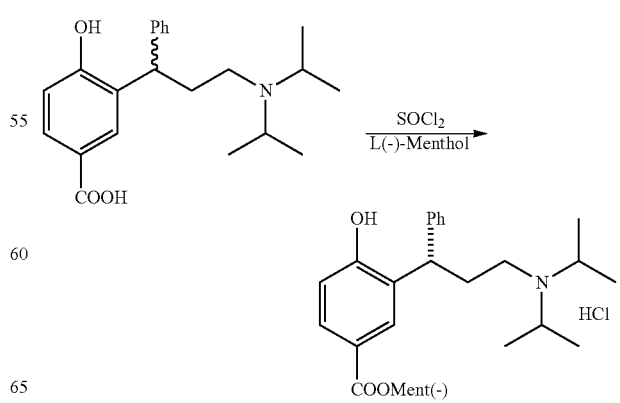

Racemic 3-(3-N,N'-diisopropylamino-1-phenyl-propyl)-4-hydroxy-benzoic acid (10 g, 28 mmol) was dissolved in 100 ml of dichloromethane under inert atmosphere, at a temperature of about 10-15° C. and 2.6 ml of thionyl chloride (36 mmol, 1.3 eq) and a few drops of DMF were added thereto. The reaction mixture was stirred at room temperature for about one hour until completion of the reaction was observed by HPLC.

L-(−)-menthol (11.8 g, 75.2 mmol, 2.68 eq) was added in portions and the mixture was stirred at room temperature for about 18 hours.

The solvent was evaporated under reduced pressure and acetone was added. The suspended solid formed was cooled, filtered and washed with acetone to yield 4.8 g of the corresponding L-(−)-menthyl 3-(3-N,N'-diisopropylamino-1(S)-phenyl-propyl)-4-hydroxy-benzoate hydrochloride (35.0% yield) with a purity of about 100% by HPLC in relation with the other diastereoisomer (L-(−)-menthyl 3-(3-N,N'-diisopropylamino-1(R)-phenyl-propyl)-4-hydroxy-benzoate hydrochloride remaining in the mother's liquor).

$^1$H NMR (400 MHz, CDCl$_3$) δ 10.74 (s, 1H), 10.05 (s, 1H), 7.74 (d, 1H), 7.63 (dd, 1H), 7.27 (m, 4H), 7.17 (m, 1H), 6.98 (d, 1H), 4.70 (m, 1H), 4.35 (t, 1H), 3.54 (m, 2H), 2.90 (m, 2H), 2.47 (m, 1H), 1.92 (m, 1H) 1.76 (m, 1H), 1.64 (m, 2H), 1.44 (m, 2H), 1.23 (dd, 6H), 1.16 (dd, 6H), 1.05 (m, 2H), 0.84 (dd, 6H), 0.67 (d, 3H).

Example 4

Preparation of (R)-3-(3-N,N'-diisopropylamino-1-phenyl-propyl)-4-hydroxy-benzoic acid

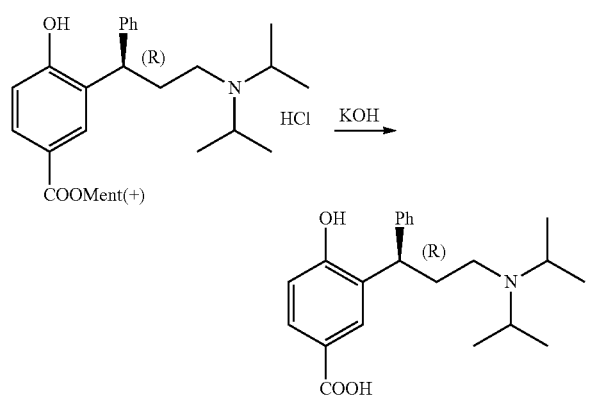

D-(+)-menthyl 3-(3-N,N'-diisopropylamino-1(R)-phenyl-propyl)-4-hydroxy-benzoate hydrochloride (3 g, 5.6 mmol) was added to a solution of 5 g of potassium hydroxide (89.1 mmol) in 18 ml of methanol and 2 ml of water. The reaction mixture was heated under reflux for about 15-24 hours until completion of the reaction was observed by HPLC. The reaction mixture was then cooled, the solvent was partially evaporated under reduced pressure, 30 ml of water were added and the pH was adjusted to 7-8 with sulfuric acid. The resulting slurry was filtered and the mother liquor was extracted with dichloromethane. The aqueous phase was partially evaporated under reduced pressure to afford a suspension, which was filtered to yield 1.6 g (80% yield) of (R)-3-(3-N,N'-diisopropylamino-1-phenyl-propyl)-4-hydroxy-benzoic acid. Specific rotation [α]=−57.2° (c=0.5 in methanol/water (80/20)).

The isolated product was enantiomerically pure by chiral HPLC.

$^1$H NMR (400 MHz, DMSO) δ 7.77 (d, 1H), 7.59 (dd, 1H), 7.23 (m, 4H), 7.11 (m, 1H), 6.81 (d, 1H), 4.34 (t, 1H), 2.99 (m, 2H), 2.34 (m, 2H), 2.08 (m, 2H), 0.87 (d, 12H).

Example 5

Preparation of (S)-3-(3-N,N'-diisopropylamino-1-phenyl-propyl)-4-hydroxy-benzoic acid

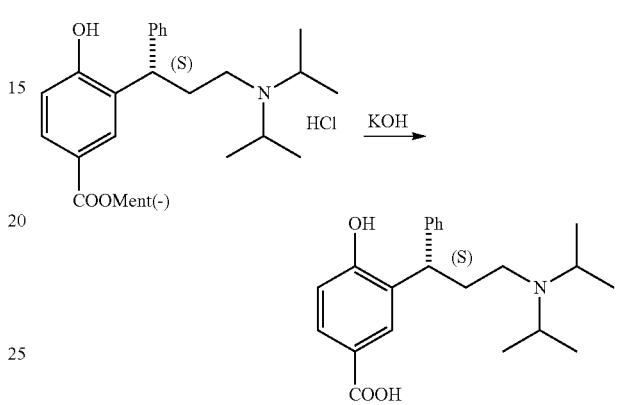

L-(−)-menthyl ester of 3-(3-N,N'-diisopropylamino-1(S)-phenyl-propyl)-4-hydroxy-benzoate hydrochloride (3 g, 5.6 mmol) was added to a solution of 5 g of potassium hydroxide (89.1 mmol) in 18 ml of methanol and 2 ml of water. The reaction mixture was heated under reflux for about 15-24 hours until completion was observed by HPLC. The reaction mixture was then cooled, the solvent was evaporated partially under reduced pressure, 30 ml of water were added and the pH was adjusted to 7-8 with sulfuric acid. The resulting slurry was filtered and the mother liquor was extracted with dichloromethane. The aqueous phase was partially evaporated under reduced pressure to afford a suspension, which was filtered to yield 1.5 g (75% yield) of (S)-3-(3-N,N'-diisopropylamino-1-phenyl-propyl)-4-hydroxy-benzoic acid. Specific rotation [α]=+62.0° (c=0.5 in methanol/water (80/20)).

The product isolated was enantiomerically pure by chiral HPLC.

$^1$H NMR (400 MHz, DMSO) δ 7.77 (d, 1H), 7.59 (dd, 1H), 7.23 (m, 4H), 7.11 (m, 1H), 6.81 (d, 1H), 4.34 (t, 1H), 2.99 (m, 2H), 2.34 (m, 2H), 2.08 (m, 2H), 0.87 (d, 12H).

Example 6

Obtention of (R)-3-(N,N'-diisopropylamino-1-phenyl-propyl)-4-isobutyryloxy-benzoic acid

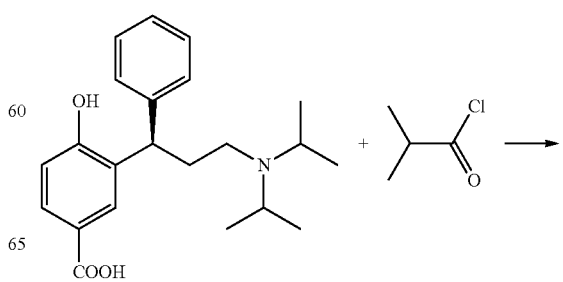

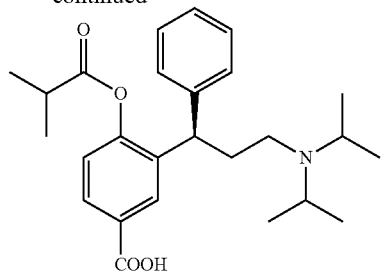

Triethylamine (8 ml, 2.05 eq) and isobutyryl chloride (3.2 ml, 1.1 eq) were added to a suspension of 10 g of (R)-3-(3-N,N'-diisopropylamino-1-phenyl-propyl)-4-hydroxy-benzoic acid in 50 ml of dichloromethane maintaining the temperature at 10-15° C. The resulting mixture was warmed to 20-25° C., stirred until completion was observed and then cooled. 50 ml of water were added and the pH was adjusted to 7.0-7.5. The solvent was evaporated under reduced pressure and methylisobutylketone (MIK, 30 ml) was added. The product began to crystallize and 30 ml of heptane were slowly added to increment the amount of solid precipitated. The resulting suspension was filtered and dried giving rise to 10.2 g (85% yield).

The isolated product was enantiomerically pure by chiral HPLC.

$^{13}$C RMN (DMSO): 18.6, 18.8, 1901, 19.2, 33.5, 34.2, 40.7, 43.5, 50.1, 122.5, 126.4, 127.7, 128.3, 128.5, 128.9, 132.5, 135.9, 143.2, 150.6, 167.8, 174.6.

Example 7

Obtention of Fesoterodine Through Chemoselective Reduction

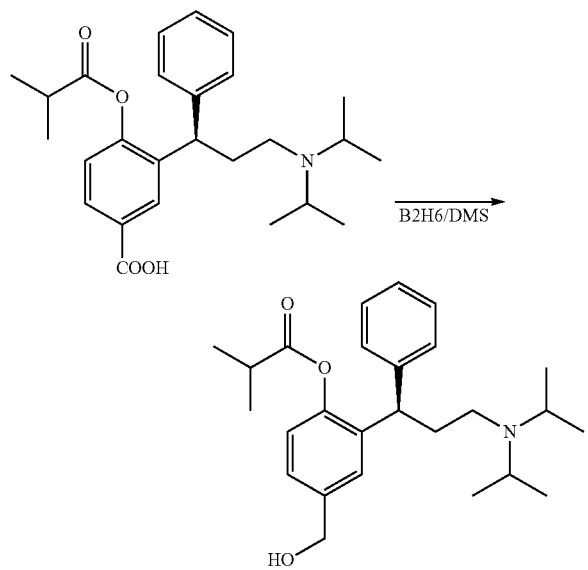

A 2 M solution of borane-dimethylsulfide complex in THF (36 ml, 3.0 eq.) was slowly added to a suspension of (R)-3-(N,N'-diisopropylamino-1-phenyl-propyl)-4-isobutyryloxy-benzoic acid (10 g) in THF (50 ml) at 10-15° C. The resulting mixture was warmed and stirred at 20-25° C. until its completion (4-8 h). The resulting mixture was slowly added over 100 ml of a water/AcOH solution (AcOH in an amount of 8%) and maintained with stirring until complete hydrolysis. Ethyl acetate (50 ml) was added and the resulting two phases were separated. The aqueous phase was extracted once with 100 ml of $CH_2Cl_2$ and two more times with 2×50 ml of $CH_2Cl_2$. The resulting organic phase was neutralized to pH 7.5-8.0, the solvent was evaporated under reduced pressure and methylethylketone (MEK, 50 ml) was added. The resulting mixture was added over a suspension formed by 2.72 g of fumaric acid (1.0 eq) and MEK (50 ml) and seeded with crystals of Fesoterodine. The suspension was cooled to 0/5° C. and maintained at this temperature for about 8 hours, filtered and dried to obtain 7.5 g of the final product with a yield of 60.5%.

The isolated product was enantiomerically pure by chiral HPLC.

Example 8

Obtention of R(+)-2-(3-Diisopropylamino-1-phenyl-propyl)-4-hydroxymethyl-phenol

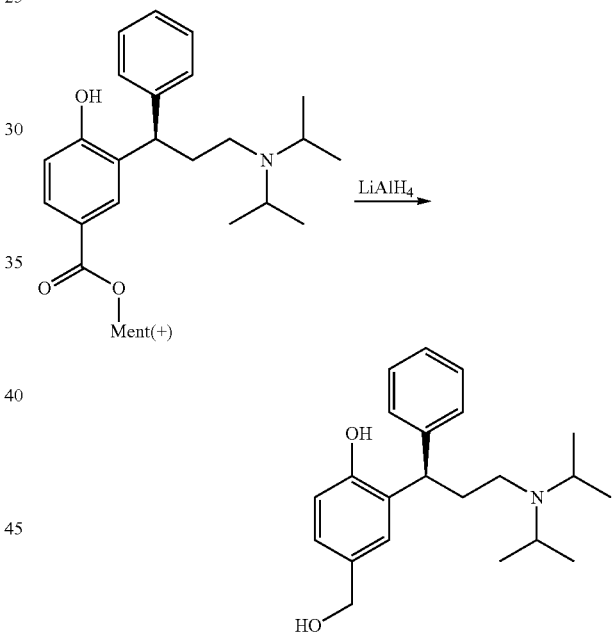

D-(+)-menthyl 3-(3-N,N'-diisopropylamino-1(R)-phenyl-propyl)-4-hydroxy-benzoate hydrochloride (9.64 g, 18 mmol) was suspended in 60 ml of $CH_2Cl_2$ and 40 ml of water, and a solution of 10% NaOH was slowly added with stirring until pH of about 7-8. The organic phase was separated and the solvent was evaporated under reduced pressure. The obtained residue was dissolved in THF (50 ml) and the resulting solution was slowly added into a suspension of lithium aluminium hydride (1.4 g, 37 mmol) in THF (50 ml) at a temperature of about 0-5° C. Stirring was continued during 4 h at the same temperature and the mixture was slowly brought to about 20-25° C. and maintained at that temperature for about 6-10 h. To the resulting mixture cooled at 0-5° C., was added in succession: 50% THF/water (2.8 ml), 15% aqueous NaOH (4.2 ml) and THF/water (3 ml). The white suspension formed was left under stirring for 2-4 h. The obtained salts were filtered and washed with 2×10 ml of THF and the resulting mother liquors was evaporated under reduced pressure, redissolved with CH$_2$Cl$_2$ and washed with water. The separated organic phase was evaporated under reduced pressure to obtain a residue that was washed several times with heptane to remove some impurities, giving rise to 5 g of the final product (83% yield).

Example 9

Obtention of Fesoterodine Through Ester Formation

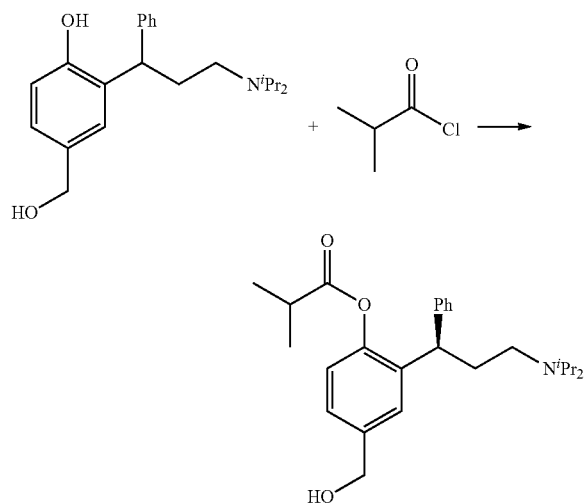

A solution of R(+)-2-(3-Diisopropylamino-1-phenylpropyl)-4-hydroxymethyl-phenol (4 g, 10.36 mmol) in toluene (16 ml) was added to a solution of NaOH (1.24 g, 31 mmol) in water (15 ml). The obtained mixture was slowly added under strong stirring to a solution formed by isobutyryl chloride (1.5 ml, 14.32 mmol) and toluene (12 ml). After completion of the addition, the mixture was left under stirring for 20 minutes, the phases were separated and the solvent of the organic phase was evaporated under reduced pressure to obtain 4.5 g of an oily residue (95% yield).

Example 10

Obtention of Fesoterodine Hydrochloride

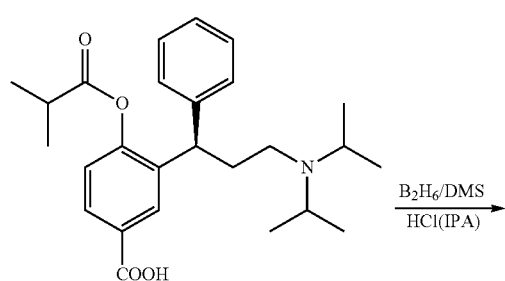

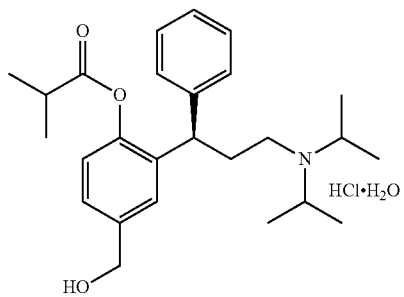

A 2 M solution of borane-dimethylsulfide complex in THF (36 ml, 2.0 eq.) was slowly added to a suspension of (R)-3-(N,N'-diisopropylamino-1-phenyl-propyl)-4-isobutyryloxy-benzoic acid (10 g) in THF (25 ml) at 20-25° C. The resulting mixture was stirred at room temperature until its completion (8-10 h). A 5% aqueous solution of Acetic Acid (50 ml) was added at 20-25° C. The resulting mixture was stirred at room temperature until its completion (10-12 h). The solvent was evaporated under reduced pressure at a temperature below 35° C. The mother liquor was extracted three/four times with dichloromethane (25-30 ml each time). The organic phases were mixed and evaporated under reduced pressure. A 7% aqueous solution of NaHCO$_3$ (50 ml) was added and stirred to afford a pH 8.0-8.5. The organic phase was separated and evaporated under reduced pressure and acetone was added. Water 5.0 ml was added and an isopropyl alcohol solution of hydrochloric acid (4.0-6.0 ml) was added to afford a pH 3.5-4.0 at 10-15° C. Then diisopropyl ether (14.0-16.0 ml) was added and the mixture formed was stirred 2-3 h to afford the crystallization of the product, then diisopropyl ether (60.0-64.0) ml was added slowly and the mixture was stirred for 2-3 h. Finally the resulting solid was filtered and washed with acetone/diisopropyl ether (20 ml) to yield 8.2 g of Fesoterodine hydrochloride monohydrate.

Example 11

Obtention of Fesoterodine Fumarate

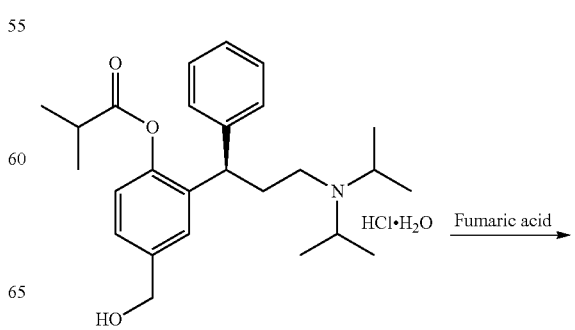

-continued

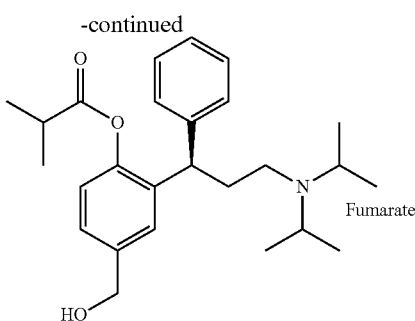

A 7% solution of aqueous NaHCO₃ (25 ml) was added to a suspension of Fesoterodine Hydrochloride monohydrate (5 g) in dichloromethane (50 ml) at 10-15° C. The resulting mixture was stirred at room temperature and the two phases were separated. The organic phase was evaporated under reduced pressure; acetone (10 ml) was added twice and evaporated under reduced pressure to afford a Fesoterodine base solution. The Fesoterodine base solution was added over an acetone/fumaric acid suspension (10 ml/1.25 g) at 15-20° C. Diisopropyl ether 5 ml was added at 10-15° C. and the suspension was stirred to allow crystallization for 1-2 h, then diisopropyl ether 5 ml was added and the suspension stirred for 1-2 h. Finally diisopropyl ether (30 ml) was added and the suspension stirred for another 1-2 h. The suspension was filtered off and the crystallized product was washed with acetone/diisopropyl ether (10 ml), to yield 5.1 g of the corresponding Fesoterodine Fumarate.

What is claimed is:

1. A compound of formula (IV) or (IV')

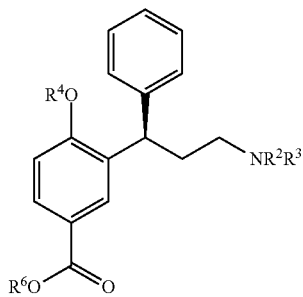

(IV)

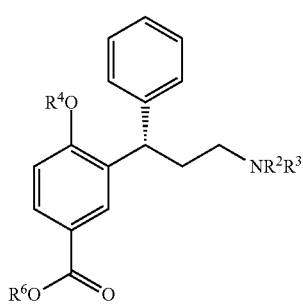

(IV')

wherein, $R^2$ and $R^3$, independently of one another, are selected from H and $C_1$-$C_6$ alkyl, or together form a ring of 3 to 7 members with the nitrogen to which they are bound; $R^4$ is hydrogen or a hydroxyl protecting group; and $R^6$ is a chiral group; or a solvate or salt thereof.

2. A compound according to claim 1, wherein $R^6$ is the residue of (+)-menthol or (−)-menthol.

3. A compound according to claim 1 selected from the group formed by

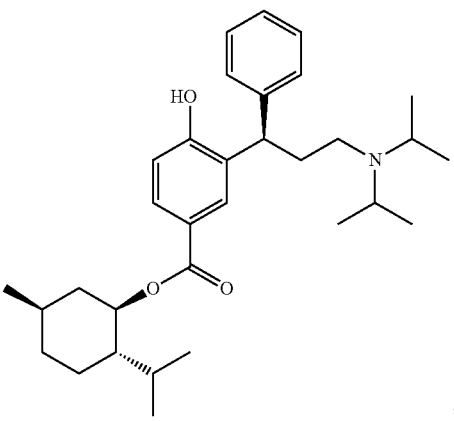

,

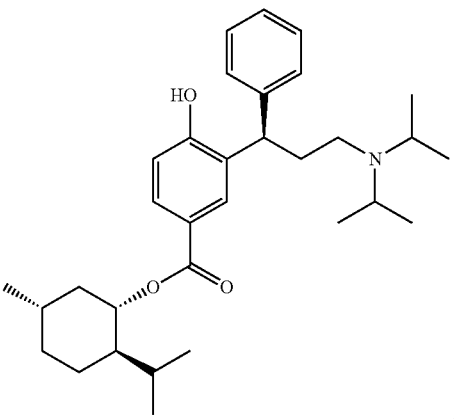

,

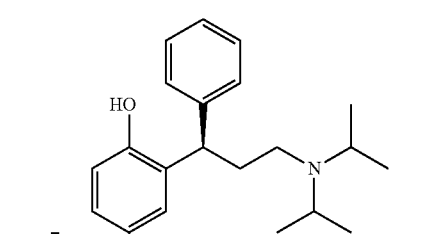

,

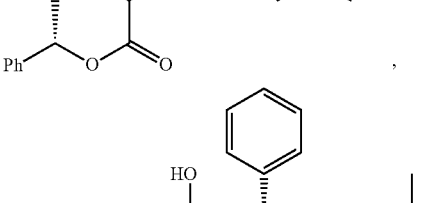

,

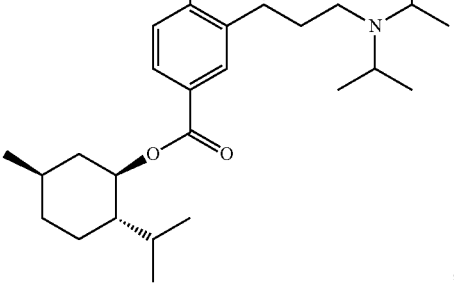

,

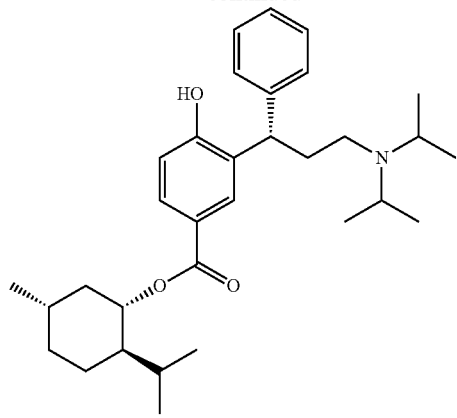
,
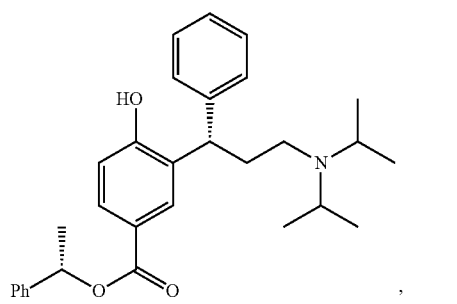
,
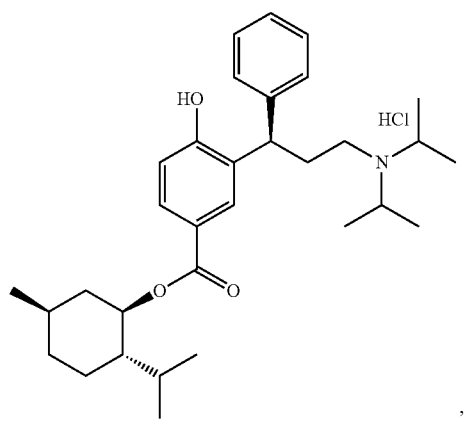
,
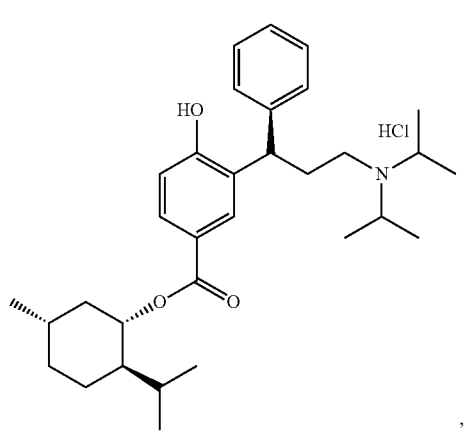
,
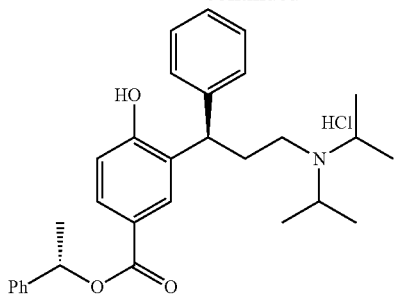
,
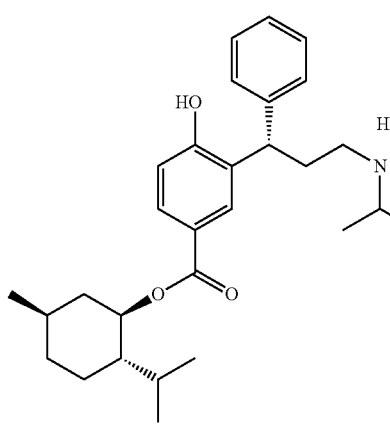
,
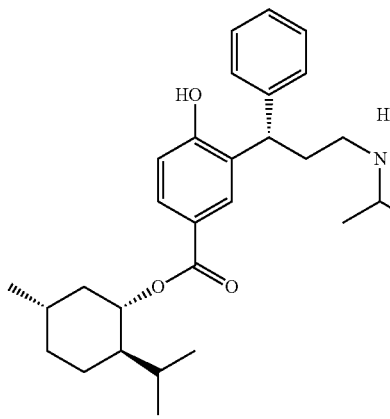
, and
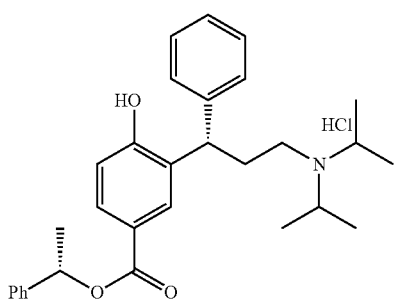
,
or a solvate thereof.
4. A compound according to claim 3 selected from the group formed by

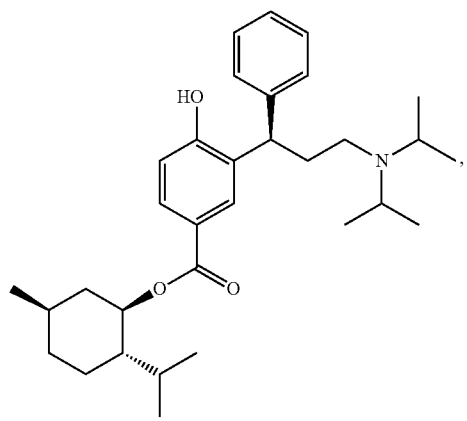
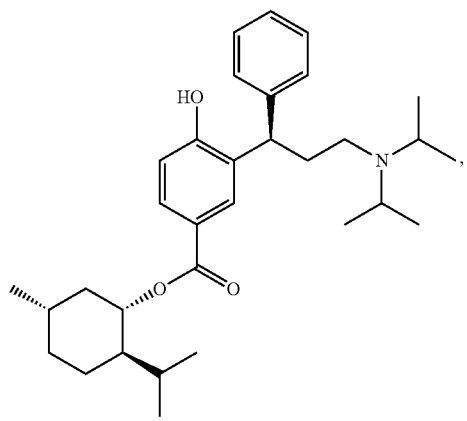
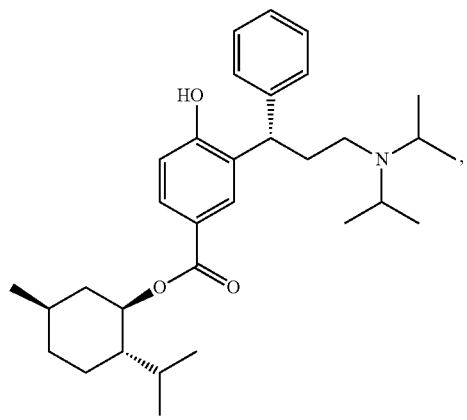
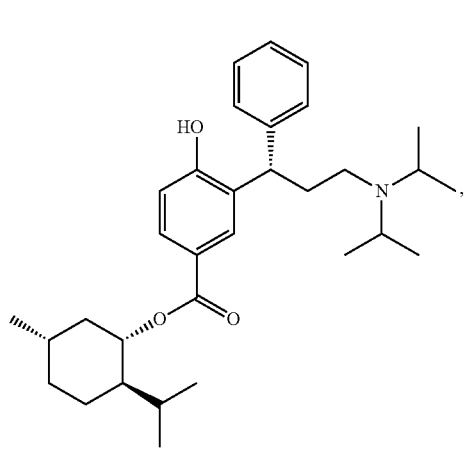
-continued
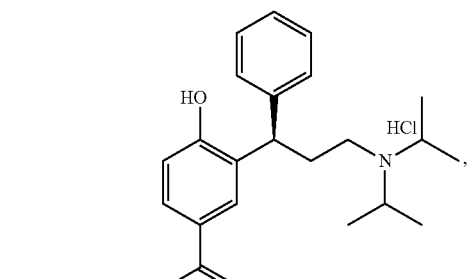
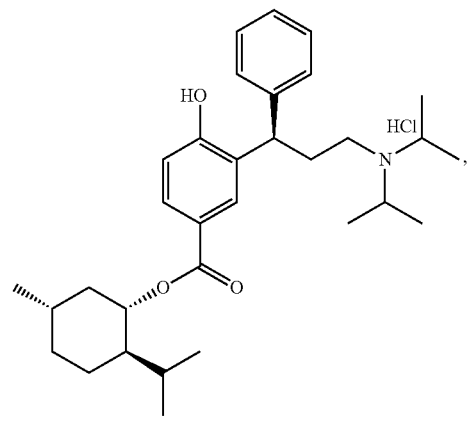
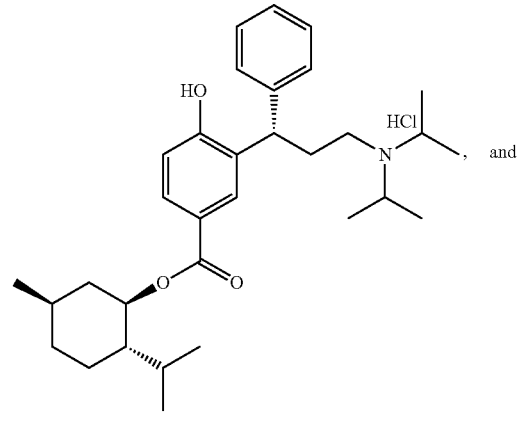
, and
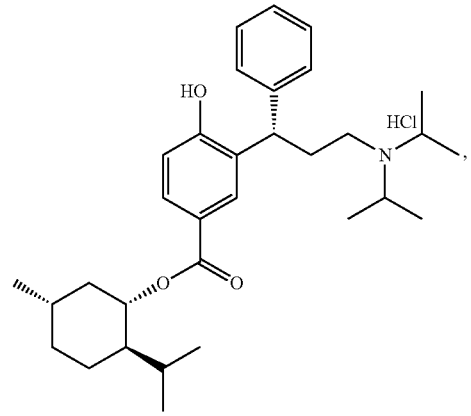
or a solvate thereof.

5. A process for preparing a compound of formula (IV) or (IV') as defined in claim 1, or a solvate or salt thereof, the process comprising reacting a compound of formula (II), or a solvate or salt thereof,

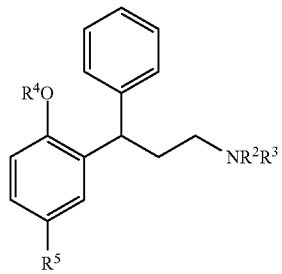
(II)

wherein
$R^2$, $R^3$ and $R^4$ are as defined in claim 1; and
$R^5$ is selected from —C(O)Cl, —C(O)Br, —C(O)OH, —C(O)OR', —C(O)OCOR' and CN, wherein R' is selected from $C_1$-$C_6$ alkyl, $C_1$-$C_6$ haloalkyl, aryl and arylalkyl;
with an optically active chiral alcohol of formula (III)

 (III)

wherein $R^6$ is as defined in claim 1.

6. The process according to claim 5, wherein the compound of formula (IV) or (IV'), or the solvate or salt thereof, is further (b) separated; and (c) converted into a compound of formula (I) or (I'), respectively, or a solvate or salt thereof

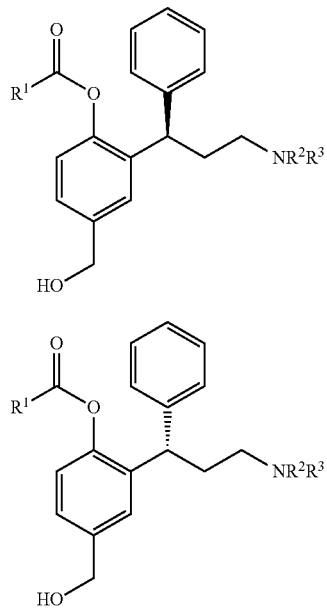

wherein
$R^1$ is $C_1$-$C_6$ alkyl; and
$R^2$ and $R^3$ as defined in claim 5.

7. The process according to claim 6, wherein the chiral alcohol of formula (III) is a chiral secondary alcohol wherein the hydroxyl group is attached directly to a chiral centre.

8. The process according to claim 7, wherein the chiral alcohol of formula (III) is selected from (D)-(+)-menthol, (L)-(−)-menthol and (S)-1-phenylethanol.

9. The process according to claim 8, wherein the chiral alcohol of formula (III) is selected from (D)-(+)-menthol and (L)-(−)-menthol.

10. The process according to claim 6, wherein $R^2$ and $R^3$ are independently selected from $C_1$-$C_6$ alkyl.

11. The process according to claim 9, wherein $R^1$, $R^2$ and $R^3$ are isopropyl.

12. The process according to claim 6, wherein $R^4$ is hydrogen.

13. The process according to claim 6, wherein $R^5$ is selected from —C(O)Cl and —C(O)Br.

14. The process according to claim 6, wherein the compound of formula (IV) or (IV'), or a solvate or salt thereof, is converted into a compound of formula (I) or (I'), or a solvate or salt thereof, by a process comprising:

(a) subjecting compound of formula (IV) or (IV'), or a solvate or salt thereof, to a reduction reaction to obtain a compound of formula (V) or (V'), respectively, or a solvate or salt thereof,

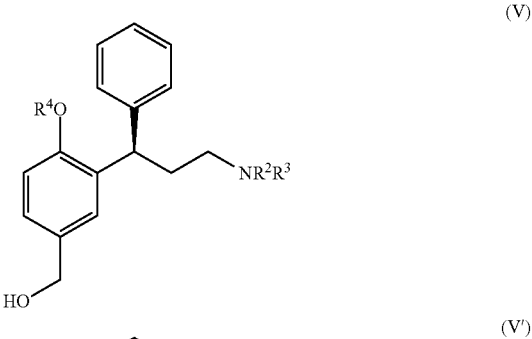

wherein $R^2$, $R^3$ and $R^4$ are as defined in claim 5;
(b) if $R^4$ is a hydroxyl protecting group, deprotecting it either before or after step (a); and
(c) subjecting a compound of formula (V) or (V'), or a solvate or salt thereof, wherein $R^4$ is hydrogen to an esterification reaction with a compound of formula (VI)

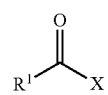
(VI)

wherein
$R^1$ is as defined in claim 6, and
X is selected from Cl, Br, OH, OR" and OCOR", wherein R" is selected from $C_1$-$C_6$ alkyl, $C_1$-$C_6$ haloalkyl, aryl and arylalkyl;

to obtain a compound of formula (I) or (I'), or a solvate or salt thereof;
or by a process comprising:
(a) subjecting compound of formula (IV) or (IV'), or a solvate or salt thereof, to a hydrolysis reaction to obtain a compound of formula (VII) or (VII'), or a solvate or salt thereof, (VII)

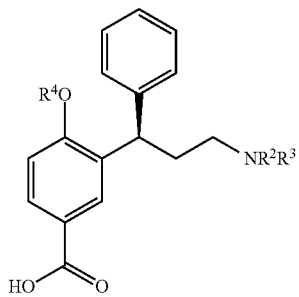

(VII')

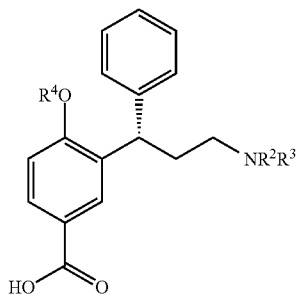

wherein $R^2$, $R^3$ and $R^4$ are as defined in claim 5;
(b) if $R^4$ is a hydroxyl protecting group, deprotecting it either before or after step (a);
(c) subjecting a compound of formula (VII) or (VII'), or a solvate or salt thereof, wherein $R^4$ is hydrogen to an esterification reaction with a compound of formula (VI)

(VI)

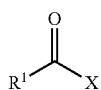

wherein
$R^1$ is as defined in claim 6, and
X is selected from Cl, Br, OH, OR" and OCOR", wherein R" is selected from $C_1$-$C_6$ alkyl, $C_1$-$C_6$ haloalkyl, aryl and arylalkyl,
to obtain a compound of formula (VIII) or (VIII'), or a solvate or salt thereof, (VIII)

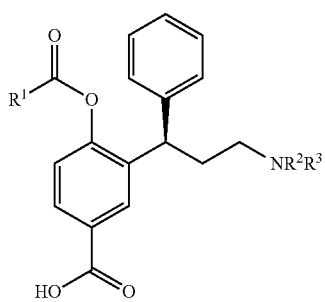

(VIII')

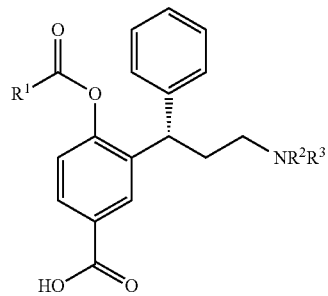

wherein $R^1$, $R^2$ and $R^3$ are as defined in claim 5; and
(d) subjecting compound of formula (VIII) or (VIII'), or a solvate or salt thereof, to a chemoselective reduction to obtain a compound of formula (I) or (I') or a solvate or salt thereof.

15. The process according to claim 6, wherein the compound of formula (I) or (I') in the free amine form is further converted into a salt thereof by treatment with an acid.

16. The process according to claim 6, wherein the compound of formula (I) or a salt or solvate thereof is selected from the group consisting of Fesoterodine, Fesoterodine fumarate, Fesoterodine hydrochloride, and a solvate thereof.

17. The process according to claim 6, wherein the compound of formula (I) or a salt or solvate thereof is selected from the group consisting of Fesoterodine, and an enantiomer, solvate or salt thereof, which comprises:
(a) reacting a compound of formula (IIa), or a solvate or salt thereof, (IIa)

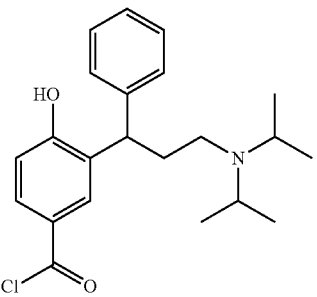

with an optically active chiral alcohol of formula (III)

$R^6$—OH     (III)

to yield a compound of formula (IVa) and the diastereoisomer, or a solvate or salt thereof, (IVa)

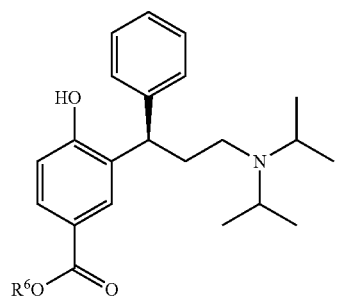

wherein R⁶ is as defined in claim 5;
(b) separating the compound of formula (IVa) or the diastereoisomer, or a salt or solvate thereof; and
(c) converting the compound of formula (IVa), or the diastereoisomer, solvate or salt thereof, into a compound of formula (I), or an enantiomer, solvate or salt thereof.

18. The process according to claim 17, wherein the compound of formula (IVa), or a diastereoisomer, solvate or salt thereof, is converted into Fesoterodine, or an enantiomer, solvate or salt thereof, by a process comprising:
(a) subjecting compound of formula (IVa), or a diastereoisomer, solvate or salt thereof, to a reduction reaction to obtain a compound of formula (Va), or an enantiomer, solvate or salt thereof,

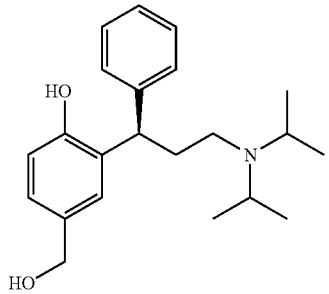

(Va)

(b) subjecting compound of formula (Va), or an enantiomer, solvate or salt thereof, to an esterification reaction with a compound of formula (VIa)

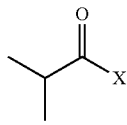

(VIa)

wherein X is selected from Cl, Br, OH, OR" and OCOR", wherein R" is selected from $C_1$-$C_6$ alkyl, $C_1$-$C_6$ haloalkyl, aryl and arylalkyl;
or by a process comprising:
(a) subjecting compound of formula (IVa), or a diastereoisomer, solvate or salt thereof, to a hydrolysis reaction to obtain a compound of formula (VIIa), or an enantiomer, solvate or salt thereof,

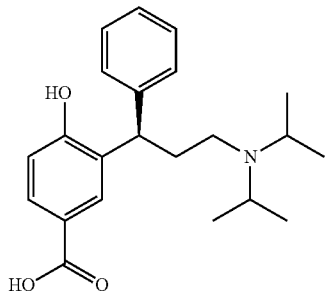

(VIIa)

(b) subjecting compound of formula (VIIa), or an enantiomer, solvate or salt thereof, to an esterification reaction with a compound of formula (VIa)

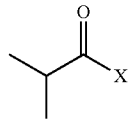

(VIa)

wherein X is selected from Cl, Br, OH, OR" and OCOR", wherein R" is selected from $C_1$-$C_6$ alkyl, $C_1$-$C_6$ haloalkyl, aryl and arylalkyl,
to obtain a compound of formula (VIIIa), or an enantiomer, solvate or salt thereof,

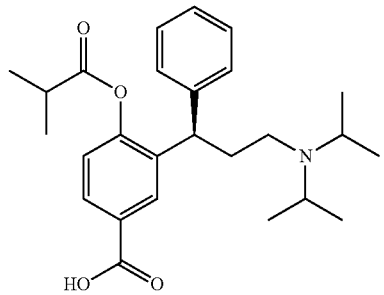

(VIIIa)

(c) subjecting compound of formula (VIIIa), or an enantiomer, solvate or salt thereof, to a chemoselective reduction.

19. The process according to claim 17, wherein Fesoterodine in the free amine form is further converted into a salt thereof.

20. The process according to claim 19, wherein Fesoterodine is further converted into Fesoterodine fumarate, Fesoterodine hydrochloride, or a solvate thereof.

21. A compound of formula (IIa)

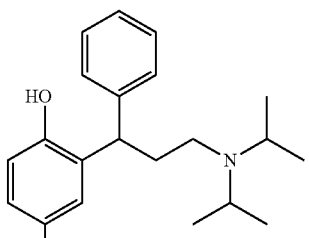

(IIa)

or a solvate or salt thereof.

22. The process according to claim 6, wherein the compound of formula (I) or a salt or solvate thereof is selected from a group consisting of Fesoterodine hydrochloride monohydrate and a solvate thereof.

23. The process according to claim 19, wherein Fesoterodine is further converted into Fesoterodine hydrochloride monohydrate, or a solvate thereof.

* * * * *